US005380713A

United States Patent [19]

Balasubramanian et al.

[11] Patent Number: 5,380,713
[45] Date of Patent: Jan. 10, 1995

[54] PEPTIDE ALDEHYDES AS ANTITHROMBOTIC AGENTS

[75] Inventors: Neelakantan Balasubramanian; Denis R. St. Laurent, both of Hartford, Conn.

[73] Assignee: Bristol-Myers Squibb Company, New York, N.Y.

[21] Appl. No.: 226,219

[22] Filed: Apr. 11, 1994

Related U.S. Application Data

[63] Continuation of Ser. No. 741,023, Aug. 6, 1991, abandoned.

[51] Int. Cl.$^6$ .................. A61K 37/00; A61K 37/02; C07K 9/06; C07K 5/08
[52] U.S. Cl. .................................... 514/18; 514/19; 546/153; 546/348; 548/146; 548/492; 548/535; 562/70; 562/445; 562/556; 562/575
[58] Field of Search ............... 514/18, 19; 546/153, 546/348; 548/146, 492, 535; 562/70, 445, 556, 575

[56] References Cited

U.S. PATENT DOCUMENTS

| | | | |
|---|---|---|---|
| 4,316,889 | 2/1982 | Bajusz et al. | 514/18 |
| 4,399,065 | 8/1983 | Bajusz et al. | 514/18 |
| 4,478,745 | 10/1984 | Bajusz et al. | 514/18 |
| 4,703,036 | 10/1987 | Bajusz et al. | 514/18 |
| 5,053,392 | 10/1991 | Klein et al. | 514/19 |
| 5,055,450 | 10/1991 | Edwards et al. | 514/19 |
| 5,106,835 | 4/1992 | Albright et al. | 514/18 |
| 5,153,176 | 10/1992 | Abe et al. | 514/18 |
| 5,157,022 | 10/1992 | Barbul | 514/18 |

FOREIGN PATENT DOCUMENTS

| | | |
|---|---|---|
| 0479489-A2 | 8/1992 | European Pat. Off. . |
| 2091270-A | 7/1982 | United Kingdom . |
| 2244994 | 12/1991 | United Kingdom . |

OTHER PUBLICATIONS

Kawamura, Kondo, Maeda and Umezawa, *Chem Pharm Bull*, 17: 1902–1909 (1969).
McConnell, et al, *J. Med. Chem.*, 33: 86–93 (1990).
Bajusz, et al., *J. Med. Chem.*, 33: 1729–35, (1990).

Primary Examiner—Ronald W. Griffin
Attorney, Agent, or Firm—Prabodh I. Almaula

[57] ABSTRACT

This invention relates to novel arginine aldehydes, their salts and hydrates, which compounds selectively exhibit serine proteases inhibitory activity, are highly stable in aqueous solutions, and are useful for anti-trypsin and anti-thrombin activity.

47 Claims, 1 Drawing Sheet

▲ = COMPOUND OF EXAMPLE 14
● = D-Phe-Pro-Arg-aldehyde SULFATE
○ = CONTROL

PEPTIDE ALDEHYDES AS ANTITHROMBOTIC AGENTS

This is a continuation of application Ser. No. 07/741,023, filed Aug. 6, 1991, now abandoned.

BACKGROUND OF THE INVENTION 1. Field of Inventions

This invention relates to novel arginine aldehydes, their salts and hydrates, which compounds selectively exhibit serine proteases inhibitory activity, are highly stable in aqueous solutions, are useful for anti-trypsin and anti-thrombin activity, and to a process for the preparation thereof. 2. Description of the Art Arginine aldehydes of specific structure are known to inhibit the actions of proteolytic enzymes such as serine, cysteine, trypsin, thrombin, papain and plasmin. Umezawa et al, reported the proteolytic activity of naturally occurring leupeptins. Leupeptins are derivatives of simple tripeptide whose structures have an aldehydic group instead of a carboxyl group in the arginine moiety. (Umezawa et al, *Chem Pharm Bull,* 17: 1902–1909 (1969)). Recently, McConnell et al, published several analogs of leupeptins which inhibited a number of serine proteases. However, leupeptins are not selective among enzymes of similar substrate specificities, thus limiting their usefulness as therapeutic agents (McConnell, et al, *J. Med. Chem.,* 33:86–93 (1990)).

Thrombin, a key enzyme in the blood coagulation cascade, is involved in the conversion of fibrinogen into fibrin gel during the blood clotting process. U.S. Pat. No. 4,316,889, issued Feb. 25, 1982, U.S. Pat. No. 4,399,065, issued Aug. 16, 1983, and U.S. Pat. No. 4,478,745, issued Oct. 23, 1984 disclose arginine aldehydes derived from amino acids (D-Phe-Pro-Arg-aldehydes) as thrombin inhibitors. However, the recent published data by Bajusz et al, (*J. Med. Chem.* 33, 1725-35, (1990)) clearly indicate that these aldehydes are not stable in aqueous medium. They undergo a series of intramolecular reactions to produce inactive heterocyclic compounds. See also U.S. Pat. No. 4,703,036, issued Oct. 2, 1987, and *J. Med. Chem.* 33: 1729–1735, (1990).

Trypsin is secreted by the pancreas in an inactive form, thus preventing autodigestion. Protease inhibitors in the pancreas and pancreatic juice provide protection against autodigestion.

Further disclosed is a process for the preparation of the arginine aldehydes of the present invention.

The present invention discloses novel arginine aldehydes, their salts and hydrates which are stable in aqueous media, selectively inhibit trypsin and thrombin over other serine proteases such as plasmin, and which are useful for anti-trypsin and anti-thrombin activity.

SUMMARY OF INVENTIONS

An object of the present invention is to provide novel arginine aldehydes.

An object of the present invention is to provide novel arginine aldehydes which selectively inhibit the proteolytic enzymes thrombin and trypsin.

A further object of the present invention is to provide novel arginine aldehydes which are highly stable in aqueous medium.

Another object of the present invention is to provide novel arginine aldehydes which have anti-thrombin activity and thus are useful as anti-thrombotic agents.

A further object of the present invention is to provide novel arginine aldehyde which have antitrypsin activity and thus are useful as agents to treat pancreatitis.

Yet another object of the present invention also provides a process for the preparation of the compounds of the present invention.

A further objective of the present invention is to provide prodrug carbamates of the compounds of the present invention, preferably (acyloxy) alkyl carbamates, benzyl carbamates, alkyl carbamates.

The present invention also provides useful intermediates, and process for their preparation.

DESCRIPTION OF THE INVENTION

Figure 1:
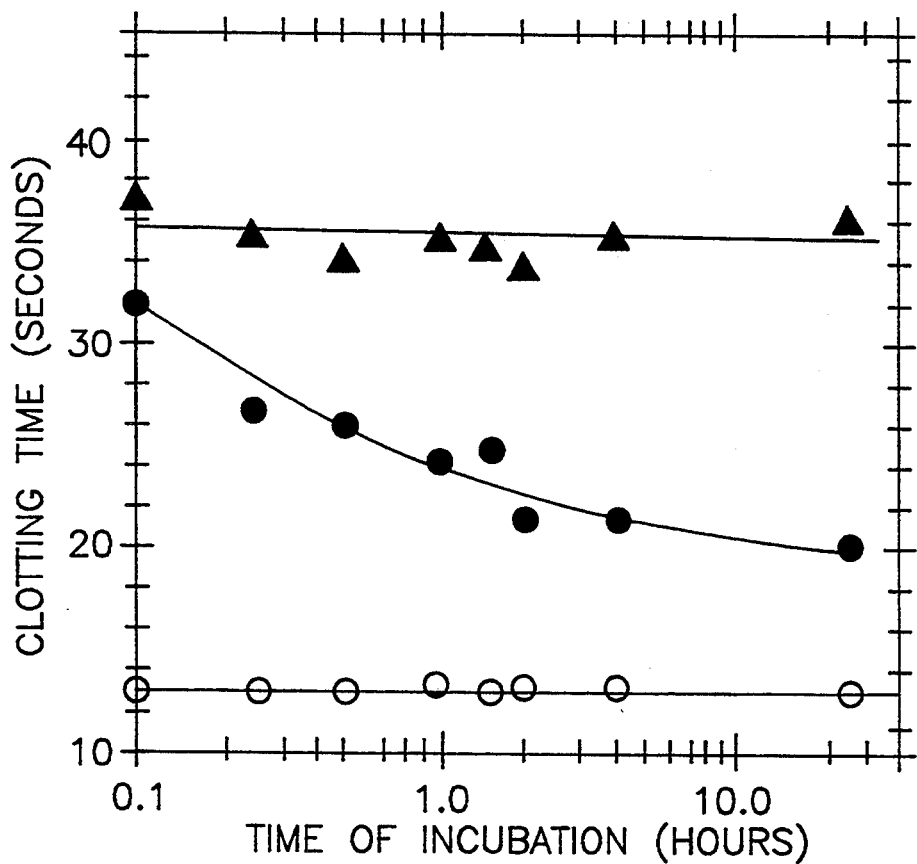
FIG. 1 illustrates the effect of incubation of compound of Example 14 at 40° on thrombin clotting times measured using pooled human plasma.

The present invention provides novel arginine aldehyde compounds, their salts and hydrates thereof which are stable in aqueous solution, which are selective inhibitors of the proteolytic enzymes thrombin and trypsin, and which are useful in the treatment of thrombosis and hemeostasis.

The compounds of the present invention, have the general Formula (I)

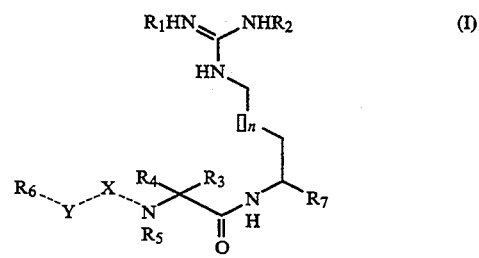

wherein $R_1$ and $R_2$ are independently or together hydrogen, or COOR, preferably hydrogen, wherein R is hydrogen, lower alkyl, benzyl or $CH(OCOCH_3)CH_3$;

$R_3$ and $R_4$ are independently or together hydrogen, lower alkyl, benzyl, phenyl, or cycloalkyl of 3 to 7 carbon atoms, wherein the phenyl and cycloalkyl ring are unsubstituted or substituted with lower alkyl or lower alkoxy and other optionally substituted aromatic heterocyclic groups, preferably lower alkyl; additionally, $R_3$ and $R_4$ may be linked together to form a cycloalkyl of 3 to 7 carbon atoms, wherein the cycloalkyl ring is unsubstituted or substituted with lower alkyl or lower alkoxy, or $R_3$ and $R_4$ may be linked together to form a phenyl or other aromatic ring, wherein the carbonyl amide residue and the substituted nitrogen residue form two substituents of the aromatic ring such that one of the substituents shifts to another carbon, as for example

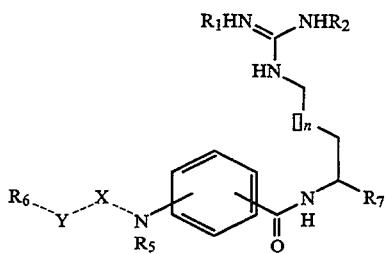

$R_5$ hydrogen, or lower alkyl, additionally, $R_5$ and $R_3$ or $R_4$ may be linked together to form a heterocyclic ring of 3 to 7 carbon atoms, preferably 5 carbon, most preferably 4 carbon, wherein the heterocyclic ring is unsubstituted or substituted with lower alkyl or lower alkoxy;

X is carbonyl, $(CH_2)_m$, or $SO_2$, preferably carbonyl;

Y is $(CH_2)_m$, $CH_2CH-NHR_8$, or $CH_2NH-R_8$ preferably $(CH_2)_m$ most preferably $CH-NH-R_8$, wherein $R_8$ is lower alkyl, phenyl, benzyl, aminoiminomethyl $R_1$ and $R_2$ as described above cycloalkyl ring of 3–7 carbon atoms, or $SO_2R_9$, preferably $SO_2R_9$, wherein $R_9$ is lower alkyl, cycloalkyl ring of 3–7 carbon atoms, unsubstituted or substituted phenyl, or unsubstituted or substituted naphthyl, preferably substituted naphthyl;

provided that when Y is $(CH_2)_m$, the $R_6$ is $(CH_2)_m R_{10}$, wherein $R_{10}$ is substituted or unsubstituted phenyl, pyridinyl, thienyl, naphthyl, quinolinyl or cycloalkyl rings of 3 to 7 carbon atoms, preferably phenyl, wherein the substitutent is independently selected from lower alkyl, lower alkoxy, amino, or halogens; when Y is $CH-NHR_8$, then $R_6$ is hydrogen or benzyl; and when Y is $CH_2CH-NHR_8$, then $R_6$ is hydrogen, substituted or unsubstituted phenyl, pyridinyl, thienyl, quinolinyl, naphthyl, or cycloalkyl rings of 3 to 7 carbon atoms, wherein the substituent is independently selected from lower alkyl, lower alkoxy, amino, and halogen;

$R_7$ is CHO, $CH_2OH$, or COOH, preferably CHO;

n is −1, −2, 0, 1, 2, 3, or 4; and m is 0, 1, 2, or 3.

As used herein and in the claims, except where otherwise indicated, "lower alkyl" means branched or unbranched hydrocarbon chain having, unless otherwise noted, one to six carbon atoms, including but not limited to methyl, ethyl, propyl, isopropyl, n-propyl, butyl, sec-butyl, isobutyl, n-butyl, and the like.

The term prodrug as used herein and in the claims (unless the context indicates otherwise) denotes an analog of an active drug which after administration is capable of undergoing hydrolysis of the carbamate moiety or oxidative cleavage of the carbamate moiety so as to release active free drug. The physiologically hydrolyzable carbamates serve as prodrugs by being hydrolyzed in the body to yield the parent drug per se.

The following common abbrevations of the amino acids are used throughout this specification: Arg—arginine; Gly—glycine; Phe—phenylalanine; pro—proline; Val—valine.

As the compounds of the present invention may possess one or more asymmetric carbon atoms, the invention includes all of the possible enantiomeric and diastereomeric forms of the compounds of the Formula (I). As described herein and in the claims, most of the starting amino acids used in this invention are the naturally occurring (L) amino acids. However, in several instances the pure (D) enantiomers of the natural amino acids or the (D) and (L) mixtures or the racemate were also used. The final aldehydic compounds exist in equilibrium with their open chain, cycli-aminal, and hydrated form.

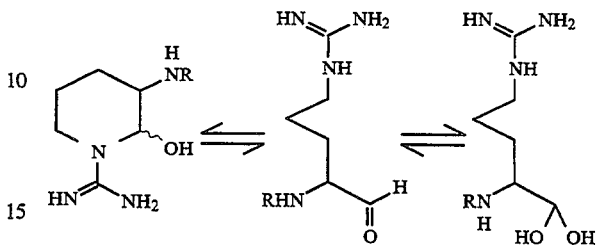

These appear to contain varying amounts of solvent as ascertained mainly by elemental analysis, and magnetic resonance spectroscopy methods (NMR). The present invention is intended to include solvates of the compounds of Formula (I). In most cases, the solvate, generally is water and, preferably, one to three moles of water. For most cases, the examples below give the amount of solvent when appropriate in the analysis and the melting points are those of the solvated product unless otherwise indicated.

Method of Preparation

The general process for the preparation of the compounds disclosed in this invention is described in Schemes I and II. Intermediate lactam III was prepared from the readily available $N^\alpha$-Boc arginine as described below in Example 1. Treatment of the lactam III with gaseous HCl provided the amino lactam IV, in 95% yield (Example 2). Compound V, which was necessary to couple with lactam IV, was obtained from the readily available t-Butyl ester of proline and the appropriate acid. Coupling of V and IV under the standard conditions for the peptide coupling such as DPPA/NEt$_3$, HOBT, hydroxy succinimide, DCC, CDT, and most preferably, isobutyl chloroformate/NEt$_3$ (as described is Scheme I), gave the intermediate lactam VII. Alternatively, lactam VII may be obtained (as described in Scheme II) by directly coupling lactam IV with readily available Nt-Boc-proline, under the standard peptide coupling methods mentioned above, preferably using isobutyl chloroformate/NEt$_3$ to give lactam X as described below in Example 3. The free amine XI was obtained by treating X with gaseous HCl (Example 9). Coupling of the Pro-Arg lactam with the I0 appropriate acid (see below) preferably under the isobutyl chloroformate conditions (Example 5) gave the lactam VII in good yield. Hydride reduction, preferably using LAH/THF, of the lactam VII after work up (Example 6) provided the aminal VIII. Removal of the protecting group under hydrogenolysis condition, preferably with H$_2$/Pd/C at 1 atm. in the presence of an acid such as HCl, H$_2$SO$_4$ gave the desired product I. (Example 7).

Most of the arginine aldehydes disclosed in this invention are prepared employing the procedures described in Scheme I and/Scheme II. The compounds of formula VII wherein R is defined in Table 1 are synthesized most preferably utilizing the reaction sequences outlined in Scheme I.

Further, the compounds of formula VII wherein the R group is defined in Table I may be obtained most preferably using the synthetic routes described in Scheme II.

Most of the starting acids were prepared by previously described procedures and/or are known and these preparations are described in the art, while many others are commercially available. For example, preparation of the 2-aminophenyl thiazole acetic acid used in one of the examples was prepared as described by Knott, et al, *J. Chem. Soc.*, 455, (1945). Similarly, the 2-amino-4,5-diphenyl imidazole was prepared according to the procedure in the literature. (*J. Org. Chem.* 44, 818 (1977)). The 4,5-diphenyloxazole acids were prepared by the conventional manner, well known to those skilled in the art. The fully saturated 3-cyclohexylpropyl compound was prepared from the corresponding commercially available aldehyde and the appropriate proline derivative employing a known reductive amination procedure.

The prodrug forms of the preferred embodiment of the compounds of Formula I may be prepared by the general procedures described in *J. Med. Chem.*, 31, 318, (1988). Preferably these carbamate groups may also be introduced at an early stage of the synthetic sequence as described in Scheme I and II.

SCHEME I

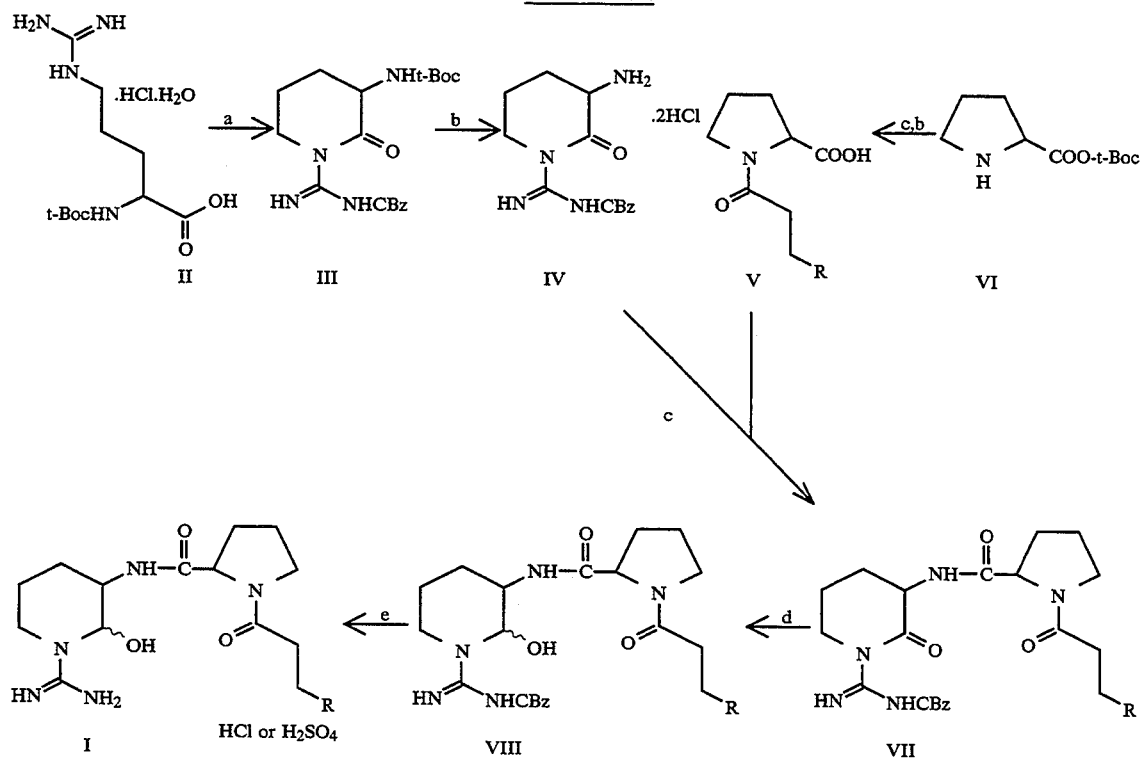

a) NEt₃/Benzyl chloroformate/THF/−20° C.
b) HCl/EtOAc/0° C.
c) isobutyl chloroformate/NEt₃, THF/−20° C./RCO₂H or RCOCl
d) LAH/THF/−20° C.
e) H₂/Pd/C/1 atm and 1.0N HCl or 0.5N H₂SO₄.

SCHEME II

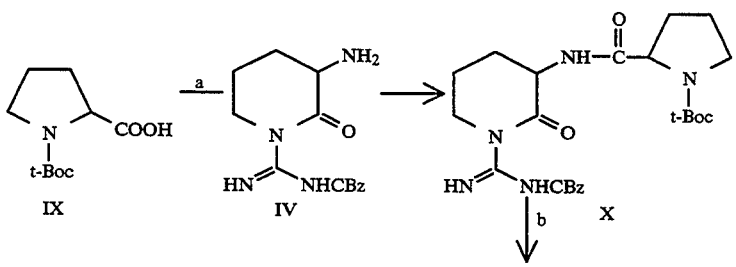

SCHEME II

-continued a) isobutyl chloroformate/NEt₃/THF/−20° C.
b) HCl/EtOAc/0° C.
c) isobutyl chloroformate/NEt₃/THF/−20° C./the acid Biological Testing 1. Enzyme Assays for the Inhibition of Thrombin The following reagents were used in these assays:

Thrombin assay buffer: 145 mM NaCl, 5 mM KCl, 30 mM N-2-hydroxyethyl piperazine-N'-2-ethanesulfonic acid, pH 7.4, 1 mg/ml polyethylene glycol (PEG-8000).

3 mM D-Phe-Pip-Arg-p-nitroanilide (s-2238) in $H_2O$

3 U/ml purified human α-thrombin dissolved in thrombin assay buffer.

Inhibitors to be tested were dissolved in $H_2O$, methanol, or DMSO just prior to use.

Assay Procedure

To each well in a 96-well microtiter plate, 270 μl of assay buffer was added. Human α-thrombin (10 μl of 3 U/ml) was added, then 10 μl of inhibitor were added and mixed. The samples were incubated at room temperature for a defined period of time (3 minutes for initial $IC_{50}$ determinations). The enzymatic reaction was started with 10 μl of 3 mM s-2238 substrate and continued at room temperature. The change in optical density was measured at 405 nm. A kinetic microplate reader (Molecular Devices Corporation $v_{max}$) was used to measure the change in optical density over time.

Results are reported in Table I as $IC_{50}$ values, i.e., the drug concentration in mole/liter which caused 50% inhibition of the enzyme activity (after incubation of the drug with the enzyme for 3 minutes). Table I shows that the compounds of Formula I are potent inhibitors (in vitro) of the enzymes thrombin and trypsin.

2. Enzyme Assays for the Inhibition of Trypsin

The following reagents were used in these assays:

Trypsin assay buffer: 2 mM $CaCl_2$, 50 mM Tris/Cl pH 8.0.

3 mM Z-Val-Gly-Arg-pNA (Chromzyme TRY) dissolved in water.

6 μg/ml of purified bovine pancreatic trypsin dissolved in trypsin assay buffer.

Inhibitors to be tested were dissolved in $H_2O$, methanol or DMSO just prior to use.

Assay Procedure

To each well in a 96-well microtiter plate, 270 μl of assay buffer was added. Bovine trypsin (10 μg/ml) was added. Inhibitor (10 μl) was added, mixed, and then incubated at room temperature for 3 minutes. The enzymatic reaction was started with 10 μl of 3 mM Z-Val-Gly-Arg-pNA substrate. The change in optical density was measured at 405 nm at room temperature. A kinetic microplate reader (Molecular Devices Corporation $v_{max}$) was used to measure the change in optical density over time.

Results are reported in Table I as $IC_{50}$ values, i.e., the drug concentration in mole/liter which caused 50% inhibition of the enzyme activity (after incubation of the drug with the enzyme for 3 minutes).

Procedure for Determining the Concentration Required for Doubling Thrombin Clotting Time—Clotting Time Assays The following reagents were used in these assays:

Owren's Veronal Buffer: 125 mM NaCl, 28.4 mM sodium barbital, pH 7.35.

Human citrated plasma obtained from human volunteers or citrated plasma obtained from dosed animals (prepared as described below).

25 NIH Units/ml human α-thrombin in thrombin buffer for use with rat plasma. 10 NIH Units/ml human α-thrombin in thrombin buffer for use with human plasma.

Preparation of the Citrated Plasma

Human Plasma: Blood from human volunteers was drawn into vacutainer tubes containing one tenth final volume of 0.129M (3.8%) buffered citrate (16 mg Sodium Citrate $2H_2O$ and 2.1 mg citric acid per milliliter of $H_2O$). The blood was centrifugated at 3500 rpm (480 xg) for 15 minutes at room temperature (using a Sorvall RT 6000B centrifugate). The plasma was removed, pooled, and aliquoted into small tubes which were stored frozen for later use.

Dosing: Test compound was prepared just prior to dosing. Routinely the drugs are dissolved in water. Occasionally other vehicles are used, such as PEQ-200 stock solutions are vortex mixed and animals are dosed p.o. using a 3 ml syringe with an 18–19 gauge oral gavage needle or i.p. injection.

Blood Drawing for Rats: After the appropriate time period, the animals were ether-anesthetized, and blood was drawn by cardiac puncture using 333 μl of 3.8% sodium citrate per 3 ml blood. After all of the samples were obtained, the tubes were centrifuged at 1,500 rpm for 15 minutes as described for the human blood samples.

Clotting Time Measurement

Clotting times were determined by pipetting 0.1 ml of Owren's buffer (pre-warmed to 37° C.) and 0.1 ml of human or rat plasma into yellow sample cuvettes. For studies with human plasma 10 U/ml human thrombin (10 ml) was placed in the reservoir assembly station of the MLA 700. (Medical Laboratory Automation, Electra 700 Reservoir Assembly). For rat studies, the human thrombin concentration was 25 U/ml. The cuvettes were vortexed and then placed on the MLA 700 sample wheel. The coagulation timer (MLA 700) automatically dispenses 0.1 ml human thrombin into the sample in each cuvette. Detection of the fibrin clot was determined optically by the MLA 700.

Studies were performed to determine the concentration of drug which caused a doubling of the clotting time (DTT) in human plasma. From standard curves of thrombin activity added to the sample versus the clotting time, the concentration of drug which caused a doubling of the thrombin clotting time corresponded to inhibition of approximately ½ of the added thrombin clotting activity. Results are reported below.

In separate studies, compounds were dosed orally (p.o.) to three rats in each study group. These compounds prolonged clotting time as measured ex vivo (by the method described above). Results of such study are presented in Table II. Table II shows that the compounds of the present invention are effective, after dosing orally, in prolonging thrombin clotting time and therefore, are efficient anti-thrombin agents. Consequently, they are useful in controlling blood coagulation in mammals including humans.

CLOTTING TIME AFTER INCUBATION OF COMPOUND IN WATER AT 40° C.

Fresh blood was drawn from two human donors into vacutainer tubes containing buffered sodium citrate (16 mg sodium citrate and 2.1 mg citric acid per 4.5 ml of blood). The tubes were centrifuged immediately at 1920×g for 15 minutes to obtain fresh platelet poor plasma. The plasma was pooled and 10 ml aliquots were divided into three test tubes. Two tubes were frozen and maintained at −20° C. for future use and one tube was kept on ice throughout testing.

The compound of Example 14 and D-Phe-Pro-Arg aldehyde: $H_2SO_4$ were prepared as stock solutions (50 μM) in deionized water. The compound of Example 14 was added to cuvettes in concentrations which initially caused prolongation of clotting time to approximately three times control value (final concentrations of 0.2 μM was used for Example 14 while 0.5 μM was used for D-Phe-Pro-Arg aldehyde). After the initial effect of these compounds on clotting time was determined, the compounds were placed in a 40° C. water bath for various time intervals (from 0.25–24 hours) and aliquots were withdrawn to determine the effect of the incubation on clotting time.

Clotting times were measured optically using the Medical Laboratory Automation Electra 700 (MLA 700). Test cuvettes contained 0.1 ml of pre-warmed Owren's buffer, 0.1 ml of the human plasma and 1.2 and 3.0 μl of the test compounds dissolved in water. The cuvette was then vortex mixed and placed on the MLA 700 sample wheel. Clotting time was determined at 37° C. after the addition of 0.1 ml of 10U/ml human thrombin (final concentration=3.3 U/ml).

The foregoing biological results show that the compounds of the present invention exhibit antithrombin and anti-trypsin activities, good stability, and are thus useful in controlling blood coagulation and treating pancreatitis.

The stability of the compounds of the present invention were measured or described in the biological procedures. The data is presented for Example 14 and is compared to the known compound D-Phe-Pro-Arg aldehyde: $H_2SO_4$. The data demonstrate that the diamino shown here is more stable than the corresponding D-phe compound. ( FIG. 1 ) .

TABLE I(a)

BIOLOGICAL EVALUATION AND THE METHOD OF PREPARATION OF SUBSTITUTED ARGINALS.

| Method of Preparation | R group | DCT (μM) | In Vitro EC$_{50}$ Thrombin (μM) | Trypsin (μM) |
|---|---|---|---|---|
| A | CH$_3$—⟨phenyl⟩—SO$_2$ | 150 | 150 | — |
| A | ⟨phenyl⟩—CH$_2$—C(D)(H$_2$N)—C(O) | >200 | >200 | — |
| A | ⟨phenyl⟩—CH$_2$—C(H$_2$N)—C(O)—NH—C(H$_3$C)(D)—C(O) | 1.0 | 0.15 | 0.11 |
| A | ⟨phenyl⟩—CH$_2$—C(D)(H$_2$N)—C(O)—N⟨piperidine-C(O), D,L⟩ | 0.28 | 0.049 | 0.1 |
| A | Ph$_2$C=N—(CH$_2$)$_n$C(O)  n = 2<br>n = 4 | 100<br>200 | 37.5<br>25 | 0.78<br>0.58 |

TABLE I(a)-continued
BIOLOGICAL EVALUATION AND THE METHOD OF PREPARATION OF SUBSTITUTED ARGINALS.

Structure:

$$\text{OHC-CH(NHR)-CH}_2\text{CH}_2\text{CH}_2\text{-NH-C(=NH)-NH}_2 \cdot x\text{HCl} \cdot x\text{H}_2\text{O}$$

| Method of Preparation | RHN group | DCT (μM) | In Vitro EC$_{50}$ Thrombin (μM) | Trypsin (μM) |
|---|---|---|---|---|
| A | Boc-proline-C(O)- | 45 | 150 | — |
| A | 5-(dimethylamino)naphthalene-1-sulfonyl-proline-C(O)- | 15 | 18.75 | — |
| B | D-Tyr-Pro-C(O)- (H$_2$N, HO-phenyl) | 5.0 | 7.04 | 0.13 |
| A | β-amino-β-phenyl-propionyl-Pro-C(O)- (D,L) | 0.5 | 0.29 | 0.03 |
| A | Ph-CH(NH$_2$)-(D,L)-CH$_2$-C(O)-NH-CH(Ph)(D,L)-CH$_2$-C(O)-N-Pro-C(O)- | 3.0 | 4.69 | — |

TABLE I(b)
BIOLOGICAL EVALUATION OF AND THE METHOD OF PREPARATION OF SUBSTITUTED ARGINALS.

Structure:

$$\text{RHN-CH(CHO)-CH}_2\text{CH}_2\text{CH}_2\text{-NH-C(=NH)-NH}_2 \cdot x\text{HCl} \cdot x\text{H}_2\text{O}$$

| Method of Preparation | RHN group | DCT (μM) | In Vitro EC$_{50}$ Thrombin (μM) | Trypsin (μM) |
|---|---|---|---|---|
| B | β-amino-phenylalanyl(D,L)-Pro-C(O)- | 2.0 | 1.76 | 0.26 |
| A | D-(guanidino)-phenylalanyl-Pro-C(O)- | 0.5 | 0.11 | 0.2 |

TABLE I(b)-continued
BIOLOGICAL EVALUATION OF AND THE METHOD OF PREPARATION OF SUBSTITUTED ARGINALS.

| Method of Preparation | Structure | DCT (μM) | In Vitro EC₅₀ Thrombin (μM) | Trypsin (μM) |
|---|---|---|---|---|
| B | [D-Phe-Gly-Pro arginal with H₂N-C(O)- on side chain] | 0.1 | 0.08 | 1.2 |
| A | [Ph,Ph-vinyl guanidine-CH₂-C(O)-] | — | 7.9 | — |
| B | [indanyl-NH-CH₂-C(O)-Pro-C(O)] | — | 0.4 | — |
| A | [2-(3-aminopropyl)phenyl-SO₂-NH-CH₂-C(O)-Pro-C(O)] | — | 0.060 | — |
| A | [dimethylamino-vinyl substituted aminophenyl-SO₂-NH-CH₂-C(O)-Pro-C(O)] | — | 0.030 | — |
| B | [Ph-CH₂CH₂-C(O)-Pro-C(O)] | 0.4 | 0.39 | 0.024 |
| A | [Ph-CH₂CH₂-C(O)-pipecolinyl D,L-C(O)] | — | 1.3 | 0.1 |
| A | [Ph-CH₂CH₂-C(O)-NH-C(O)] | 15 | 18.75 | 0.19 |
| B | [cyclohexyl-CH₂CH₂-C(O)-Pro-C(O)] | 0.3 | 0.15 | 0.018 |

TABLE I(b)-continued
BIOLOGICAL EVALUATION OF AND THE METHOD OF PREPARATION OF SUBSTITUTED ARGINALS.
| Method of Preparation | RHN-CHO ... xHCl.xH₂O | DCT (μM) | In Vitro EC$_{50}$ Thrombin (μM) | Trypsin (μM) |
|---|---|---|---|---|
| B | 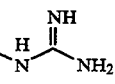 | 75 | 56 | — |
| B | 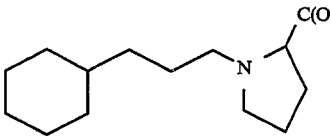 | 4.0 | 4.69 | 0.024 |
| B | 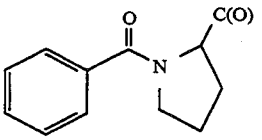 | 1.0 | 0.84 | 0.024 |
| B | 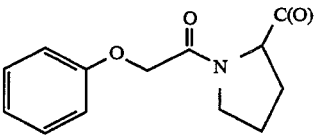 | 0.75 | 0.59 | 0.018 |
| B | 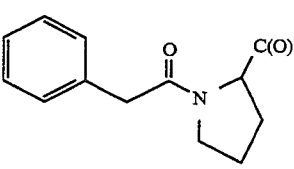 | 0.5 | 0.88 | 0.024 |
| B | 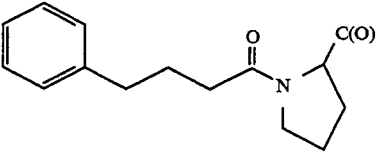 | 0.5 | 0.59 | 0.024 |
| B | 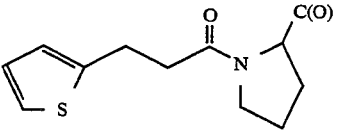 | 2.5 | 1.76 | 0.074 |
| B | 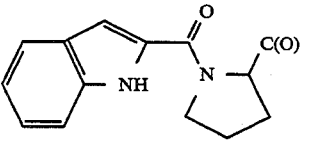 | 1.5 | 1.17 | 0.13 |
| A | 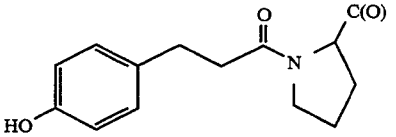 | 1.0 | 1.17 | 0.098 |

TABLE I(b)-continued
BIOLOGICAL EVALUATION OF AND THE METHOD OF PREPARATION OF SUBSTITUTED ARGINALS.

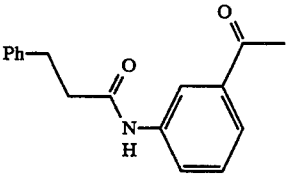

| Method of Preparation | CHO | xHCl.xH₂O | DCT (μM) | In Vitro EC₅₀ Thrombin (μM) | Trypsin (μM) |
|---|---|---|---|---|---|
| A | (structure shown) | | — | 20 | — |

TABLE II
EX VIVO CLOTTING TIME PROLONGATION MEASUREMENTS

| Compound in Example No. | DTT (mg/kg) |
|---|---|
| 8 | ~100 |
| 9 | 150 |
| 12 | 100 |
| 13 | 100 |
| 14 | 60 |
| 16 | 50 |
| 19 | 110 |

Administration of the active compounds, salts and hydrates described herein can be via any of the accepted modes of administration for systemically active therapeutic medications. These methods include oral, nasal, parenteral and otherwise systemic forms.

Depending on the intended mode of administration, the compositions used may be in the form of solid, semi-solid or liquid dosage forms, such as, for example, tablets, suppositories, pills, capsules, powders, liquids, aerosols, suspensions, or the like, preferably in unit dosage forms suitable for single administration of precise dosages. The compositions will include a conventional pharmaceutical carrier or excipient and an active compound of the Formula (I) or the pharmaceutically acceptable salts or hydrates thereof and, in addition, may include other medicinal agents, pharmaceutical agents, carriers, adjuvants, etc.

For solid compositions, conventional non-toxic solid carriers include, for example pharmaceutical grades of mannitol, lactose, starch, magnesium sterate, sodium saccharin, talcum, cellulose, glucose, sucrose, magnesium carbonate, and the like may be used. The active compound as defined above may be formulated as suppositories using, for example polyalkylene glycols, for example propylene glycol, as the carrier. Liquid pharmaceutically administrable compositions can, for example, be prepared by dissolving, dispersing, etc. an active compound as defined above and optional pharmaceutical adjuvants in a carrier, such as, for example water, saline, aqueous dextrose, glycerol, ethanol, and the like, to thereby form a solution or suspension. If desired, the pharmaceutical composition to be administered may also contain minor amounts of non toxic auxiliary substances such as wetting or emulsifying agents, pH buffering agents and the like, for example, sodium acetate, sorbitan monolaurate, triethanolamine sodium acetate, triethanolamine oleate, etc. Actual methods of preparing such dosage forms are known, or will be apparent, to those skilled in this art; for example see Remington's Pharmaceutical Sciences, Mack Publishing Company, Easton Penn., 15th Edition, 1975. The composition or formulation to be administered will, in any event, contain a quantity of the active compound(s) in an amount effective to alleviate the symptoms of the subject being treated.

Parenteral administration is generally characterized by injection, either subcutaneously, intramuscularly or intravenously. Injectables can be prepared in conventional forms, either as liquid solutions or suspensions, solid forms suitable for solution or suspension in liquid prior to injection, or as emulsions. Suitable excipients are, for example, water, saline, dextrose, glycerol, ethanol or the like. In addition, if desired, the pharmaceutical compositions to be administered may also contain minor amounts of non-toxic auxiliary substances such as wetting or emulsifying agents, pH buffering agents and the like, such as for example, sodium acetate, sorbitan monolaurate, triethanolamine oleate, etc.

For oral administration, a pharmaceutically acceptable non-toxic composition is formed by the incorporation of any of the normally employed excipients, such as, for example pharmaceutical grades of mannitol, lactose, starch, magnesium stearate, sodium saccharin, talcum, cellulose, glucose, sucrose, magnesium, carbonate, and the like. Such compositions take the form of solutions, suspensions, tablets, pills, capsules, powders, sustained release formulations and the like.

All publications cited in this specification are indicative of the level of skill of those skilled in the art to which this invention pertains. Each publication is individually incorporated herein by reference in the location where it is cited.

The following examples serve to illustrate the invention. They should not be construed as narrowing or limiting its scope.

In the following examples, all temperatures are given in degrees Centigrade. Melting points were recorded on a Thomas-Hoover capillary melting point apparatus and boiling points were measured at specific pressures (mm Hg) and both temperatures are uncorrected. Proton magnetic resonance ($^1$H NMR) spectra were recorded on a Bruker AM 300, Bruker WM 360 or Varian T-60 CW spectrometer. All spectra were determined in CDCl₃. DMSO-d₆ or D₂O unless otherwise indicated and chemical shifts are reported in δ units downfield from the internal standard tetramethylsilane (TMS) and interproton coupling constants are reported in Hertz (Hz). Splitting patterns are designated as follows: s, singlet; d, doublet; t, triplet; q, quartet; m, multiplet; br, broad peak; and dd, doublet of doublet. Carbon-13 nuclear magnetic resonance ($^{13}$C NMR) spectra were recorded on a Bruker AM 300 or Bruker WM 360 spectrometer and were broad band proton decoupled. All spectra were determined in CDCl$_3$ DMSO-d$_6$ or D$_2$O unless otherwise indicated with internal deuterium lock and chemical shifts are reported in δ units downfield from tetramethylsilane. Infrared (IR) spectra were determined on a Nicolet MX-1 FT spectrometer from 4000 cm$^{-1}$ calibrated to 1601 cm$^{-1}$ absorption of a polystyrene film and are reported in reciprocal centimeters (cm$^{-1}$). Relative intensities are indicated as follows; s(strong), m(medium) and w(weak).

Gas chromatography-mass spectra (GC-MS) were determined on a Finnigan 4500 Gas chromatography-quadruple mass spectrometer at ionization potential of 70 eV. Mass spectra were also recorded on a Kratos MS-50 instrument utilizing the fast atom bombardment (FAB) technique. The mass data are expressed in the format: parent ion (M+) or protonated ion (M+H)+.

Analytical thin-layer chromatography (TLC) was carried out on precoated silica gel plates (60F-Z54) and visualized using UV light, iodine vapors and/or staining with one of the following reagents: (a) methanolic phosphomolybdic acid (2%) and heating; (b) reagent (a) followed by 2% cobalt sulphate in 5M H and heating. Column chromatography, also referred to as flash column chromatography, was performed in a glass column using finely divided silica gel (32–63 μm on silica gel-H) and pressures somewhat above atmospheric pressure with the indicated solvents. All evaporations of solvents were performed under reduced pressure. As used herein, the term hexanes is a mixture of isomeric C$_6$ hydrocarbons as specified by the American Chemical Society, and the term "inert" atmosphere is an argon or nitrogen atmosphere unless otherwise indicated.

EXAMPLE 1

N$^\alpha$-tert-Butyloxycarbonyl-N$^\delta$-benzyloxycarbonyl-L-arginine lactam

Benzyl chloroformate (215 mL, 1.50 mol) was added dropwise to a cold (−20° C.), well-stirred solution of N$^\alpha$-tert-butyloxycarbonyl-L-arginine hydrochloride hydrate (450 g, 1.37 mol) and triethylamine (630 mL, 4.50 mol) in dry tetrahydrofuran (3.2 L). After about 1 hour at about −20° C., an additional equivalent of benzylchloroformate (215 mL, 1.50 mol) was added. The mixture was stirred further for about 1 hour before it was gradually warmed to ambient temperature over the course of about 2 hours. Following concentration of the solvent in vacuo, the residue was taken up in ethyl acetate and washed with saturated citric acid solution, saturated sodium bicarbonate solution and brine prior to drying and solvent evaporation. The aqueous phase was extracted twice more with dichloromethane and the organic extracts were treated to the same work-up conditions mentioned above. Two identical reactions were performed in tandem. Recrystallization of the residues from ethyl acetate furnished 230.98g (21.6%) of the title compound as a dry, white solid, m.p. 160°–162° C. (m.p. lit. 164°–166° C.). $^1$H NMR (CD$_3$SOCD$_3$) δ 9.62 (br s, 1H), 9.18 (br s, 1H), 7.39–7.30 (m, 5H), 7.16 (d, J=8.4 Hz, 1H), 5.07 (s, 2H), 4.39–4.27 (m, 2H), 3.64–3.56 (m, 1H), 2.08–1.99 (m, 1H), 1.84–1.63 (2m, 3H), 1.42 (s, 9H); $^{13}$C NMR (CD$_3$SOCD$_3$) ppm 176.10, 162.90, 159.58, 155.50, 137.11, 128.42, 128.03, 127.86, 78.26, 66.14, 51.94, 42.33, 28.27, 24.67, 19.92; IR (KBr, cm$^{-1}$) 3352, 3282, 2982, 1726, 1700, 1646, 1606, 1522, 1500, 1380, 1320, 1312, 1266, 1186, 1158, 1110, 814, 736, 698, 584; MS m/z (MH+) calcd 391.1981, obsd 391.1985.

Anal. Calcd for C$_{19}$H$_{26}$N$_4$O$_5$: C, 58.45; H, 6.71; N, 14.35.

Found: C, 58.48; H, 6.72; N, 14.16.

EXAMPLE 2

N$^\delta$-Benzyloxycarbonyl-L-arginine lactam Dihydrochloride

To a cold (0° C.) solution of N$^\alpha$-tert-butyloxycarbonyl-N$^\alpha$benzyloxycarbonyl-L-arginine lactam (230.98g, 0.59 mol) divided into two portions in dry dichloromethane (75 mL) was added a cold (0° C.), saturated solution of hydrogen chloride in ethyl acetate (1.0 L). The mixtures were stirred at about 0° C. for about 2 hours before ether was added. After refrigeration for about 1 hour at about 0° C., the mixtures were suction-filtered and dried. There was isolated 210.3g (97%) of the title compound as a dense, white solid, m.p. 91°–95° C. (sealed tube); $^1$H NMR (D$_2$O) δ 7.46 (s, 5H), 5.28–5.24 (m, 2H), 4.08 (m, 1H), 3.30 (m, 2H), 2.03 (br m, 2H), 1.86–1.81 (m, 2H); $^{13}$C NMR (D$_2$O) ppm 174.13, 155.38, 155.11, 136.73, 130.97, 130.91, 130.29, 70.79, 54.76, 42.75, 28.96, 25.25; IR (KBr, cm$^{-1}$) 3500–2500, 1746, 1684, 1634, 1598, 1498, 1456, 1236, 1154, 750, 698; MS m/z (MH+ −2HCl) 291.

Anal. Calcd for C$_{14}$H$_{18}$N$_4$O$_3$.2.0HCl.0.85H$_2$O: C, 44.43; H, 5.78; N, 14.81; H$_2$0, 4.05.

Found: C, 44.78; H, 5.65; N, 14.21; H$_2$O, 4.33.

EXAMPLE 3

N$^\alpha$-[(N-tert-Butyloxycarbonyl)-L-prolyl]-N$^\delta$-benzyloxycarbonyl-L-arginine lactam Isobutyl chloroformate (14.3 mL, 0.11 mol) was added dropwise to a cold (−20° C.) solution of tert-butyloxycarbonylproline (23.8 g, 0.11 mol) and N-methylmorpholine (12.1 mL, 0.11 mol) in dry dimethylformamide (200 mL). After about 0.5 hour at about −20° C., the solution was canulated into a cold (−20° C.) suspension of the title compound (40.0 g, 0.11 mol) and triethylamine (47.6 mL, 0.34 mol) in dry dimethylformamide (400 mL). The mixture was stirred at about −20° C. for about 0.5 hour before it was gradually warmed to room temperature over the course of about 3 hours. Following evaporation of the solvent in vacuo, the residue was taken up in ethyl acetate and washed with saturated citric acid solution, saturated sodium bicarbonate solution and brine prior to drying and solvent concentration. The residue was purified by column chromatography on silica gel (elution with 50% ethyl acetate in hexanes) and furnished 45.41 g (85%) of the title compound as a white foam, m.p. 64°–74° C; $^1$H NMR (CD$_3$SOCD$_3$) δ 9.59 and 9.17 (2 br s, 1H), 8.24–8.11 (m, 1H), 7.38–7.29 (m, 6H), 5.06 (s, 2H), 4.63–4.54 (m, 1H), 4.28–4.00 (m, 2H), 3.83–3.60 (m, 1H), 3.39–3.25 (m, 2H), 2.15–1.98 (m, 2H), 1.88–1.66 (m, 8H), 1.40 and 1.36 (2s, 9H); $^{13}$C NMR (CD$_3$SOCD$_3$) ppm 175.36, 172.47, 172.25, 162.83, 159.81, 159.64, 153.62, 153.33, 152.72, 137.08, 135.93, 128.48, 128.37, 128.20, 127.96, 127.80, 78.50, 66.41, 66.10, 59.97, 59.78, 59.58, 59.30, 50.73, 50.41, 46.70, 46.50, 43.54, 42.81, 42.17, 31.05, 30.04, 28.05, 25–18, 24.57, 23.80, 23.12, 19.87, 18.81, 14.11; IR (KBr, cm$^{-1}$) 3372, 2974, 1700, 1612, 1508, 1478, 1456, 1394, 1298, 1266, 1178, 1162, 1112; MS m/z (MH+) calcd 488.2509, obsd 488.2504.

Anal. Calcd for C$_{24}$H$_{33}$N$_5$O$_6$.0.10EtOAc.0.10H$_2$O: C, 58.83; H, 6.88; N, 14.06; H$_2$0, 0.36.

Found: C, 58.62; H, 6.70; N, 13.70; H₂O, 0.42.

EXAMPLE 4

N$^\alpha$-L-Prolyl-N$^\delta$-benzyloxycarbonyl-L-arginine lactam Dihydrochloride A cold (0° C.), saturated solution of hydrogen chloride in ethyl acetate (400 mL) was added to a cold (0° C.) solution of N$^\alpha$-[(*N-tert-butyloxycarbonyl)-L-prolyl*]-N$^\delta$-benzyloxycarbonyl-L-arginine lactam (44.41 g, 0.091 mol) in anhydrous dichloromethane (100 mL). The mixture was then stirred at about 0° C. for about 2 hours and at ambient temperature for about 2 hours before ether was added. After refrigeration for about 2 hours at about 0° C., the mixture was suction-filtered and afforded 41.30 g (98%) of the title compound as a dense, white powder, m.p. 125°-143° C. (sealed tube); ¹H NMR (D₂O) δ 7.43 (s, 5H), 5.28 (s, H), 5.24 (s, 1H), 4.49–4.38 (m, 1H), 4.04–3.76 (2m, H), 3.44–3.31 (2m, 3H), 2.53–2.44 (m, 1H), 2.33–1.70 (series of m, 8H); ¹³C NMR (D₂O) ppm 176.88, 175.40, 171.81, 171.70, 158.55, 136.70, 136.70, 136.62, 130.97, 130.87, 130.38, 130.28, 71.28, 70.74, 66.25, 61.70, 61.59, 54.91, 53.75, 49.57, 49.03, 48.59, 42.87, 31.76, 31.55, 29.45, 26.71, 25.73, 22.14, 21.95; IR (KBr, cm⁻¹) 3388, 3214, 3064, 2960, 1756, 1682, 1558, 1254, 1230, 1172, 754, 700; MS m/z (MH⁺ −2HCL) calcd 388.1985, obsd 388.1972.

Anal. Calcd for C₁₉H₂₅N₅O₄.2.0HCl.0.55H₂O: C, 48.53; H, 6.03; N, 14.90; H₂0, 2.11.

Found: C, 48.58; H, 6.39; N, 14.71; H₂O, 2.18.

EXAMPLE 5

N-(3-(3-Pyridyl)propanoyl)-L-proline Hydrochloride

To a cold (0° C.), nitrogen-blanketed mixture of 3-(3-pyridyl)propanoic acid (5.0 g, 33.0 mmol), triethylamine (9.2 mL, 66.0 mmol) and L-proline tert-butyl ester (5.6 g, 33.0 mmol) in anhydrous dimethylformamide (120 mL) was added dropwise diphenylphosphoryl azide (7.1 mL, 33.0 mmol) in anhydrous dimethylformamide (10 mL). The mixture was stirred at about 0° C. for about 1 hour and at ambient temperature for about 2 hours before the solvent was removed in vacuo and the residue was partitioned between ethyl acetate and water. The organic phase was separated and the aqueous phase was extracted twice more with ethyl acetate. The combined organic extracts were then washed with saturated sodium bicarbonate solution and brine prior to drying (NaSO₄) and solvent concentration. A cold (0° C.), saturated solution of hydrogen chloride in ethyl acetate (200 mL) was then added to the crude residue (7.92 g) dissolved in dry dichloromethane (10 mL). The mixture was stirred at about 0° C. for about 2 hours and at room temperature for about 4 hours before ether (150 mL) was added. After refrigeration for about 1 hour, the mixture was suction filtered and furnished 5.02 g (54%) of the title compound as a dense, white solid, m.p. 110°-132° C. (sealed tube); ¹H NMR (D₂O) 6 8.61 (s, 1H), 8.57 (d, J=5.9 Hz, 1H), 8.47–8.40 (m, 1H), 7.95–7.90 (m, 1H), 4.60–4.57 and 4.32–4.28 (2m, 1H), 3.53 and 3.45–3.27 (t and m, J=6.5 Hz, 2H), 3.10 (t, J=7.0 Hz, 2H) 2.92–2.70 (2m, 2H), 2.25–2.09 (m, 1H), 1.97–1.84 (m, 3H); ¹³C NMR (D₂O) ppm 178.02, 177.83, 174.76, 174.53, 149.12, 143.37, 142.61, 140.88, 129.00, 61.80, 61.08, 49.67, 48.75, 35.60, 32.76, 31.61, 31.05, 29.14, 28.96, 26.26, 24.08; IR (KBr, cm⁻¹) 3422, 2952, 1736, 1632, 1556, 1468, 1450, 1188, 778, 682; MS m/z (MH⁺−HCl) Calcd. 249.1239, obsd 249.1247.

Anal. Calcd for C₁₃n₁₆N₂O₃ 1.0HCl.0.50H₂O: C, 53.16; H, 6.18; N, 9.54; H₂O, 3.07.

Found: C, 50.41; H, 5.92; N, 8.91; H₂O, 2.93.

EXAMPLE 6

N$^\alpha$-[N-(3-(3-Pyridyl)propanoyl)-L-prolyl]-N$^\delta$-benzyloxycarbonyl-L-arginine lactam To a cold (0° C.), nitrogen-blanketed mixture of N-(3-(3-pyridyl)propanoyl)-L-proline hydrochloride (4.00 g, 14.05 mmol), triethylamine (6.0 mL, 42.15 mmol) and N$^\delta$-benzyloxycarbonyl-L-arginine lactam dihydrochloride (4.58 g, 14.05 mmol) in anhydrous dimethylformamide (100 mL) was added dropwise diphenylphosphoryl azide (3.0 mL, 14.05 mmol). The mixture was stirred at about 0° C. for about 1 hour and at ambient temperature for about 2 hours before the solvent was removed in vacuo and the residue was partitioned between ethyl acetate and water. The organic phase was separated and the aqueous phase was extracted twice more with ethyl acetate. The combined organic extracts were then washed with saturated sodium bicarbonate solution and brine prior to drying (Na₂SO₄and solvent concentration. Purification of the residue by flash chromatography on silica gel (elution with 80% ethyl acetate in hexanes followed by absolute ethyl acetate) furnished 2.40 g (33%) of the title compound as a white foam, m.p. 64°–70° C. ¹H NMR (CD₃SOCD₃) δ 9.15 (v br s, 1H), 8.50–8.44 (m, 1H), 8.42–8.39 (m, 1H), 8.17 and 8.04 (2d, J=8.0 Hz, 8.0 Hz, 0.5H), 7.76–7.67 (m, 1H), 7.39–7.17 (m, 6H), 5.04 (s, 2H), 4.57–4.48 (m, 1H), 4.40–4.28 (m, 1H), 4.16–4.11 (m, 0.5H), 3.70–3.33 (series of m, 3H), 2.83 (t, J=7.6 Hz, 2H), 2.65–2.45 (2m, 2H), 2.15–1.61 (series of m, 8H), 1.13 (s, 0.5H); ¹³C NMR (CD₃SOCD₃) ppm 175.47, 175.13, 172.16, 172.01, 171.93, 171.66, 170.23, 169.79, 162.84, 159.67, 159.54, 149.03, 146.47, 146.42, 137.46, 137.41, 137.11, 137.06, 136.94, 129.80, 128.44, 128.03, 127.87, 123.71, 68.59, 66.17, 59.85, 59.21, 55.91, 50.68, 50.45, 46.77, 46.54, 43.26, 42.45, 40.44, 40.17, 39.89, 39.61, 39.33, 39.06, 38.93, 38.78, 34.77, 34.63, 32.19, 31.80, 29.68, 29.49, 27.43, 27.27, 25.10, 24.73, 24.21, 22.36, 20.22, 19.91; IR (KBr, cm⁻¹) 3370, 2950, 1686, 1642, 1610, 1508, 1442, 1264, 1178, 1158, 1104; MS m/z (MH⁺) calcd 521.2512, obsd 521.2501.

Anal. Calcd for C₂₇H₃₂N₆O₅ 0.15H₂O: C, 61.98; H, 6.23; N, 16.07; H₂O, 0.52.

Found: C, 61.76; H, 6.26; N, 15.52; H₂O, 0.55.

EXAMPLE 7

N$^\alpha$-N-(3-(3-Pyridyl)propanoyl)-L-prolyl]-N$^\delta$-benzyloxycarbonyl-L-arginine aldehyde A solution of lithium aluminum hydride in tetrahydrofuran (1M, 2.25 mL, 2.25 mmol) was added dropwise to a cold (−20° C.) mixture of N$^\alpha$-[N-(3-(3-pyridyl)propanoyl-L-prolyl]-N$^\delta$-benzyloxycarbonyl-L-arginine lactam (1.95 g, 3.75 mmol) in dry tetrahydrofuran (40 mL). The mixture was stirred at about −20° C. for about 1 hour before it was neutralized with 1N hydrochloric acid (pH adjusted to 7) at about 0° C. After about 10 minutes, the mixture was suction-filtered through a pad of anhydrous sodium sulfate and concentrated- purification of the residue by flash chromatography on silica gel (elution with acetone) gave 1.21 g (57%) of the title compound as a white foam, m.p. 93°-103° C.; ¹H NMR (CD₃SOCD₃) δ 8.45–8.36 (2m, 2H), 7.99–7.76 (2m, 0.5H), 7.67–7.51 (m, 1H), 7.34–7.23 (m, 6H), 6.17–5.84 (series of m, 1H), 5.02–4.90 (m, 2H), 4.48–4.35 (m, 1H), 3.81–3.61 (m, 2H), 3.48–3.31 (m, 2H), 3.08–2.96 (m, 1H), 2.83–2.70 (m, 2H), 2.62–2.47 (2m, 2H), 1.97–1.60 (series of m, 5H), 1.50–1.42 (m, 2H), 1.13 (s, 0.5H); $^{13}$C NMR (CD$_3$SOCD$_3$) ppm 171.86, 171.62, 171.39, 171.05, 170.96, 170.10, 169.92, 169.84, 169.61, 163.14, 163.03, 161.10, 161.05, 160.36, 160.31, 149.77, 149.64, 149.61, 147.17, 137.94, 137.83, 137.00, 136.92, 136.07, 135.90, 135.84, 128.35, 128.05, 127.98, 127.81, 127.63, 126.49, 123.40, 90.41, 74.54, 73.90, 65.57, 65.47, 59.35, 59.02, 59.08, 58.80, 55.91, 48.99, 47.41, 47.25, 46.81, 46.59, 37.41, 34.89, 34.75, 32.19, 31.81, 29.68, 29.39, 29.24, 27.52, 27.32, 24.34, 24.20, 23.84, 22.49, 22.27, 1940; IR (KBr, cm$^{-1}$) 3396, 2946, 1618, 1522, 1446, 1282, 1084, 996; MS m/z (MH+) calcd 523.2669, obsd 523. 2663.

Anal. Calcd for C$_{27}$H$_{33}$N$_6$O$_5$ 0.30H$_2$O: C, 61.42; H, 6.61; N, 15.92; H$_2$O, 1.02.

Found: C, 61.66; H, 6.48; N, 15.59; H$_2$O, 1.00.

EXAMPLE 8

N$^\alpha$[N-(3-(3-Pyridyl)propanoyl)-L-Prolyl]-L-arginine aldehyde Dihydrochloride Palladium on carbon (10%, 93 mg) was added to a well-stirred, nitrogen-blanketed mixture of N$^{60}$ [N-(3-(3-pyridyl)propanoyl)-L-prolyl]-N$^\delta$-benzyloxycarbonyl-L-arginine aldehyde (935.0 mg, 1.79 mmol) and 1N hydrochloric acid (0.90 mL) in tetrahydrofuran (20 mL). The mixture was stirred at room temperature for about 5 minutes before the nitrogen blanket was removed and replaced with hydrogen at one atmosphere. After about 5 hours, an additional equivalent of 1N hydrochloric acid (0.90 mL) was added and the mixture was suction-filtered through Celite and concentrated down to dryness to give 800.1 mg (97%) of the title compound as a dense, white solid, m.p. 126°–144° C. (sealed tube, decomposes between 190°–210° C.); $^1$H NMR (D$_2$O) δ 8.69 (s, 1H), 8.65 (d, J=5.9 Hz, 1H), 8.53 (d, J=7.7 Hz, 1H), 8.01 (t, J=6.1 Hz, 1H), 4.38–4.34 (m, 1H), 4.11–3.81 (series of m, 1H), 3.63–3.51 (m, 3H), 3.18–3.14 (m, 2H), 2.95–2.80 (m, 2H), 2.27–2.21 (m, 2H), 2.00–1.50 (series of m, 5H); $^{13}$C NMR (D$_2$O) ppm 176.75, 176.00, 175.23, 174.64, 156.55, 149.10, 143.54, 142.65, 140.87, 129.02, 124.66, 118.79, 95.08, 92.48, 79.24, 78.46, 62.78, 62.54, 62.30, 55.89, 51.43, 50.00, 49.34, 45.53, 42.79, 41.94, 35.72, 31.91, 31.81, 28.92, 27.56, 26.38, 25.98, 24.82, 24.62, 22.56; IR (KBr, cm$^{-1}$) 3344–2876, 1654, 1554, 1448, 1248, 1000, 682. MS m/z (MH+ − 2HCL) calcd 89.2301, obsd 389.2305.

Anal. Calcd for C$_{19}$H$_{28}$N$_6$O$_3$ 2.0HCl.0.24H$_2$O: C, 49.01; H, 6.60; N, 18.05; H$_2$O, 0.93.

Found: C, 48.89; H, 6.51; N, 17.72; H$_2$O, 0.95.

EXAMPLE 9

Nα-[N-Benzoyl-L-prolyl]-L-arginine aldehyde Hydrochloride

A:
N$^\alpha$-[N-Benzoyl-L-prolyl]-N$^\delta$-benzyloxycarbonyl-L-arginine lactam Obtained 3.43 g (49%), white foam, m.p. 79°–87° C.; $^1$H NMR (CD$_3$SOCD$_3$) δ9.57 (br s, 1H), 9.14 (br s, 1H), 8.26–8.21 (m, 1H), 7.53–7.50 (m, 1H), 7.45–7.26 (m, 10H), 5.03 (2H), 4.65–4.31 (series of m, 2H), 4.20–4.15 (m, 1H), 3.65–3.37 (series of m, 3H), 2.25–2.00 (m, 2H), 1.99–1.65 (m, 6H); $^{13}$C NMR (CD$_3$SOCD$_3$) ppm 175.56, 175.27, 171.82, 171.76, 169.55, 168.44, 162.90, 159.64, 159.58, 137.26, 137.11, 136.79, 129.97, 129.51, 128.44, 128.26, 128.05, 127.87, 127.18, 126.74, 66.15, 61.95, 59.85, 59.77, 50.44, 49.89, 46,76, 42.94, 42.34, 31.85, 29.66, 24.94, 24.86, 24.68, 22.24, 20.85, 19.89, 19.81, 19.20, 14.16; IR (KBr, cm$^{-1}$) 3374, 2950, 1686, 1614, 1498, 1448, 1422, 1378, 1264, 1178, 1158, 1042; MS m/z (MH+) calcd 492.2247, obsd 492.2242. Anal. Calcd for C$_{26}$H$_{29}$N$_5$O$_5$: C, 60.20; H, 5.92; N, 14.52.

Found: C, 60.12; H, 5.99; N, 14.29.

B:
N$^\alpha$-[N-Benzoyl-L-prolyl]-N$^\delta$-benzyloxycarbonyl-L-arginine aldehyde Obtained 2.02 g (70%), white foam, m.p. 84–94° C.; NMR (CD$_3$SOCD$_3$) δ 8.10 ( br s, 1H ), 7.85 and 7.68 ( 2 d, J=7.8, 8.5 Hz, 1H), 7.54–7.43 (m, 2H), 7.34–7.27 (m, H), 6.10–5.65 (series of m, 2H), 5.02–4.91 (m, 2H), 4.56–4.51 and 4.34–4.31 (2m, 1H), 3.66–3.35 (series of m, 4H), 3.16–2.89 (m, 1H), 2.10–1.30 (series of m, H); $^{13}$C NMR (CD$_3$SOCD$_3$) ppm 171.71, 171.42, 171.34, 170.79, 170.43, 168.13, 163.33, 161.18, 160.51, 138.00, 137.89, 137.42, 136.98, 136.90, 129.90–126.67 (11 lines, olefinic), 74.49, 73.79, 65.49, 65.41, 59.85, 59.57, 59.30, 49.91, 48.99, 47.29, 46.98, 32.15, 29.55, 24.93, 24.66 24.25, 23.89, 22.29, 20.85, 19.41, 14.17; IR (KBr, cm$^{-1}$) 3380, 2948, 1612, 1522, 1448, 1284, 1082, 700; MS m/z (MH+) *calcd* 494.2403, obsd 494.2398.

Anal. Calcd for C$_{26}$H$_{31}$N$_5$O$_5$ 0.20EtOAc.0.30C-H$_4$O.0.40H$_2$O: C, 61.65; H, 6.61; N, 13.27; H$_2$O, 1.37.

Found: C, 61.94; H, 6.30; N, 13.29; H$_2$O, 1.62.

C: N$^\alpha$-[N-Benzoyl-L-prolyl]-L-arginine aldehyde Hydrochloride

Obtained 746 mg (91%), white solid, m.p. 110°–117° C. (sealed tube); $^1$H NMR (D$_2$O) δ 7.54–7.34 (m, 5H), 4.65–4.48 (m, 1H), 3.71–3.25 (series of m, 4H), 3.16 and 2.97 (2m, 1H), 2.38–2.33 (m, 1H), 1.97–1.25 (series of m, 7H), 1.15–0.95 (2m, 1H); $^{13}$C NMR (D$_2$O) ppm 176.59, 176.50, 176.28, 176.09, 175.90, 175.63, 174.72, 173.99, 159.52, 159.22, 158.62, 137.29, 137.14, 136.96, 136.88, 132.95, 132.57, 132.48, 130.76, 130.68, 130.63, 128.90, 128.51, 128.39, 92.52, 92.24, 79.25, 78.98, 78.51, 78.17, 65.56, 65.02, 64.44, 64.38, 64.22, 63.15, 63.07, 62.90, 62.67, 55.84, 52.95, 52.88, 51.41, 51.30, 50.24, 50.02, 49.85, 42.77, 42.71, 42.21, 42.07, 41.95, 41.78, 34.41, 34.31, 34,01, 32.08, 31.97, 29.44, 28.89, 27.64, 27.03, 26.96, 26.39, 26.28, 24.98, 24.83, 24.71, 24.67, 24.60, 24.41, 23.40, 20.65, 20.44, 16.12; IR (KBr, cm$^{-1}$) 3600–3000, 2952, 1662, 1612, 1572, 1448, 1242, 1002, 702; MS m/z (MH+HCl) calcd 360.2036, obsd 360.2029.

Anal. Calcd for C$_{18}$H$_{25}$N$_5$O$_3$.1.0HCl.0.80H$_2$O: C, 52.70; H, 6.79; N, 17.07; H$_2$O, 3.51.

Found: C, 52.42; H, 6.75; N, 16.70; H$_2$O, 2.39.

EXAMPLE 10

N$^\alpha$[N-(3-(2-Thienyl)propanoyl)-L-prolyl]-L-arginine aldehyde Hydrochloride A: 3-(2-Thienyl)propanoic acid Palladium on carbon (10%, 4.2 g) was added in one portion to a solution of 3-(2-thienyl)acrylic acid (15.59 g, 0.10 mol) in tetrahydrofuran (130 mL). The mixture was subjected to Parr hydrogenation conditions (45 psi, room temperature) for about 24 hours. Following filtration through Celite, the filtrate was concentrated down to dryness and gave a brown-colored solid which was recrystallized from water. There was isolated 9.32 g (60%) of the title compound as a mixture of white and tan colored needles, m.p. 58°–60° C. (m.p. lit. 62°–62.5°

C.); $^1$H NMR (CD$_3$SOCD$_3$) δ 12.2 (br s, 1H), 7.23–7.21 (m, 1H), 6.89–6.86 (m, 1H), 6.82–6.81 (m, 1H), 2.99 (t, J=7.4 Hz, 2H), 2.53 (t, J=7.4 Hz, 2H); 13C NMR (CD$_3$SOCD$_3$) ppm 173.42, 143.39, 126.90, 124.70, 123.72, 35.61, 24.70; IR (KBr, cm$^{-1}$) 3102–3036, 2922, 2644, 1706, 1440, 1408, 1310, 1232, 1220, 938, 848, 828, 714, 692; MS m/z (MH+) 157.

Anal. Calcd for C$_7$H$_8$O$_2$S: C, 53.83; H, 5.16.
Found: C, 53.90; H, 5.16.

B:

N$^α$-[N-(3-(2-Thienyl)propanoyl)-L-prolyl]-N$^δ$-benzyloxycarbonyl-L-arginine lactam Obtained 2.30 g (27%), white foam, m.p. 50°–57° C.; 1H NMR (CD$_3$SOCD$_3$) δ 9.55 and 9.14 (2 br s, 0.5H), 8.41 and 8.15 (2d, J=8.2, 8.0 Hz, 1H), 7.41–7.33 (m, 5H), 7.30–7.25 (m, 1H), 6.92–6.75 (m, 2H), 5.03 (s, 2H), 4.61–4.50 (m, 1H), 4.39–4.29 (2m, 2H), 3.69–3.36 (series of m, 3H), 3.02–2.96 (m, 2H), 2.64–2.47 (m, 2H), 2.16–1.56 (series of m, 9H); 13C NMR (CD$_3$SOCD$_3$) ppm 175.49, 175.33, 172.01, 171.89, 170.03, 169.63, 162.89, 162.84, 162.38, 159.68, 159.59, 143.97, 137.12, 128.43, 128.03, 127.86, 126.94, 126.91, 12477, 124.68, 123.71, 123.68, 66.15, 59.85, 59.24, 50.66, 50.47, 46.78, 46.55, 43.07, 42.45, 35.85, 35.68, 35.53, 31.80, 30.84, 29.47, 25.04, 24.76, 24.67, 24.44, 24.20, 22.37, 19.98; IR (KBr, cm$^{-1}$) 3370, 2950, 1642, 1610, 1508, 1440, 1264, 1180, 1158, 1104, MS m/z (MH+) calcd 526.2124, obsd 526.2122Anal.

Anal. Calcd for C$_{26}$H$_{31}$N$_5$O$_5$S.0.30DMF.0.20H$_2$O: C, 58.63; H, 6.13; N, 13.47; H$_2$O, 0.65.
Found: C, 58.33; H, 5.95; N, 13.37; H$_2$O, 0.39.

C:

N$^α$-[N-(3-(2-Thienyl)propanoyl)-L-prolyl]-N$^δ$-benzyloxycarbonyl-L-arginine aldehyde Obtained 0.94 g (45%), white foam, m.p. 82°–90° C.; $^1$H NMR (CD$_3$SOCD$_3$) δ (br m, 1H), 7.95–7.47 (series of m, 1H), 7.35–7.25 (m, 6H), 6.91–6.77 (m, 2H), 6.10–5.78 (series of m, 2H), 5.02–4.89 (m, 2H), 4.49–4.35 (m, 1H), 3.79–3.33 (series of m, 4H), 3.16–2.90 (m, 3H), 2.63–2.41 (2m, 2H), 2.31–1.65 (series of m, 7H), 1.46–1.38 (m, 2H); 13C NMR (CD$_3$SOCD$_3$) ppm 171.58, 171.38, 170.90, 169.72, 169.60, 163.32, 160.52, 143.99, 137.90, 128.34, 127.96, 127.77, 127.59, 126.94, 126.87, 124.76, 124.57, 123.66, 73.79, 65.60, 65.42, 59.84, 59.11, 48.99, 46.82, 46.63, 37.25, 35.71, 29.68, 29.36, 29.20, 24.70, 24.46, 24.33, 24.09, 23.87, 22.50, 22.28, 20.83, 19.40, 17.17; IR (KBr, cm$^{-1}$) 3296, 2936, 1650, 1624, 1522, 1446, 1376, 1284, 1232, 1170, 1080, 698; MS m/z (MH+) calcd 528.2281, obsd 528.2270.

Anal. Calcd for C$_{26}$H$_{33}$N$_5$O$_5$S.0.25EtOAc.0.25 MeOH.0.20H$_2$O: C, 58.32; H, 6.54; N, 12.48; H$_2$O, 0.64.
Found: C, 58.54; H, 6.42; N, 12.38; H$_2$O, 0.44.

D:

N$^α$-[N-(3-(2-Thienyl)propanoyl)-L-prolyl]-L-arginine aldehyde Hydrochloride

Obtained 586.0 mg (97%), slightly pale-yellow solid, m.p. 110°–130° C. (sealed tube); $^1$H NMR (D$_2$O) δ 7.26 (d, J=5.1 Hz, 1H), 7.00–6.97 (m, 1H), 6.91–6.88 (m, 1H), 5.43 and 5.37 (2s, 1H), 4.37–4.34 (m, 1H), 4.07–3.74 (series of m, 1H), 3.70–3.37 (m, 4H), 3.33–2.95 (2m, 4H), 2.89–2.50 (m, 2H), 2.47–2.37 (m, 1H), 2.24–2.15 (m, 1H), 2.07–1.48 (series of m, 8H), 1.20 and 0.86 (2m, 1H); NMR (D$_2$O) ppm 176.77, 176.47, 176.03, 175.59, 175.69, 159.34, 158.65, 145.54, 130.90, 129.24, 127.00, 126.04, 92.51, 79.32, 78.49, 62.99, 62.52, 62.34, 62.15, 56.13, 55.86, 51.46, 50.62, 50.19, 49.40, 42.80, 42.22, 41.936, 38.75, 38.05, 37.79, 35.79, 33.98, 32.00, 31.83, 30.12, 27.64, 26.78, 26.58, 26.39, 24.85, 24.67, 24.47, 23.90, 20.67, 15.39; IR (KBr, cm$^{-1}$) 3500–3000, 2950, 1658, 1538, 1446, 1242, 1000; MS m/z (MH+ –HCl), calcd for C$_{18}$H$_{27}$N$_5$O$_3$S: 394.1913, obsd 394.1912.

EXAMPLE 11

N$^α$-[N-(Indole-2-carbonyl)-L-prolyl]-L-arginine aldehyde Hydrochloride

A:

N$^α$[N-(Indole-2-carbonyl)-L-prolyl]-N$^δ$-benzyloxycarbonyl-L-arginine lactam

Obtained 1.18 g (22%), pale yellow solid, m.p. 122°–135° C.; $^1$H NMR (CD$_3$SOCD$_3$) δ 11.56 (s, 1H), 9.57 (br s, 1H), 9.16 (br s, 1H), 8.61–8.58 and 7.57–7.55 (2m, 1H), 8.45 (d, J=7.9 Hz, 1H), 7.64 (d, J=7.9 Hz, 1H), 7.45 (d, J=8.2 Hz, 1H), 7.36–7.26 (m, 7H), 7.21–7.16 (m, 1H), 7.06–7.02 (m, 2H), 5.04 (s, 2H), 4.64–4.57 (m, 2H), 4.42–4.24 (m, 1H), 4.05–3.89 (m, 1H), 3.66–3.61 (m, 2H), 2.23–1.59 (series of m, 8H); 13C NMR (CD$_3$SOCD$_3$) ppm 175.52, 171.82, 162.90, 161.60, 160.49, 159.80, 159.62, 137.11, 135.96, 130.73, 128.43, 128.04, 127.87, 127.44, 123.71, 121.84, 119.77, 112.28, 105.16, 66.17, 60.96, 59.85, 50.49, 48.82, 42.92, 42.49, 29.10, 24.90, 21.93, 20.83, 19.90, 14.16; IR (KBr, cm$^{-1}$) 3364, 2952, 1684, 1610, 1524, 1434, 1356, 1264, 1180, 1158, 1104, 748; MS m/z (MH+) calcd 531. 2356, obsd 531. 2332.

Anal. Calcd for C$_{28}$N$_{30}$N$_6$O$_5$.0.30EtOAc.0.10H$_2$O: C, 62.77; H, 5.89; N, 15.04; H$_2$O, 0.32.
Found: C, 62.92, H, 5.79; N, 15.35; H$_2$O, 0.32.

B:

N$^α$-[N-(Indole-2-carbonyl)-L-prolyl]-N$^δ$-benzyloxycarbonyl-L-arginine aldehyde Obtained 0.27 g (27%), white foam, m.p. 111°–133° C.; $^1$H NMR (CD$_3$SOCD$_3$) δ 11.66–11.45 (2m, 1H), 8.05 (br m, 1H), 7.92–7.90 and 6.77–6.73 (2m, 1H), 7.73–7.61 (m, 1H), 7.49–7.39 (m, 1H), 7.33–7.29 (m, 6H), 7.20–7.15 (m, 1H), 7.05–7.00 (m, 2H), 6.01–5.89 (m, 2H), 5.02–4.89 (m, 2H), 4.63 (br s, 1H), 3.90 (br m, 2H), 3.66 (br s, 1H), 3.34 (m, 1H), 3.02 (br m, 2H), 2.00–1.89 (series of m, 3H), 1.70–1.66 (m, 1H), 1.52–1.44 (m, 1H), 1.13–1.12 (m, 1H); 13C NMR (CD$_3$SOCD$_3$) ppm 171.57, 170.96, 163.34, 161.21, 160.54, 160.22, 141.62, 138.03, 137.92, 135.94, 130.89, 130.81, 130.54, 128.34, 128.13, 127.98, 127.90, 127.80, 127.62, 127.59, 127.43, 126.71, 126.51, 123.65, 121.83, 121.46, 119.74, 112.25, 105.04, 90.51, 74.16, 73.87, 66.00, 65.50, 65.45, 62.98, 60.97, 60.80, 60.51, 49.09, 48.87, 48.18, 47.33, 37.20, 29.17, 29.00, 25.05, 24.28, 23.88, 22.20, 21.60, 19.44; IR (KBr, cm$^{-1}$) 3410, 2948, 1602, 1526, 1438, 1284, 748; MS m/z (MH+), calcd for C$_{28}$H$_{32}$N$_6$O$_5$: 533.2512, obsd 533.2516.

C: N$^α$-[N-(Indole-2-carbonyl)-L-prolyl]-L-arginine aldehyde Hydrochloride

Obtained 190.7 mg (100%), tan solid, m.p. 161°–171° C. (sealed tube); $^1$H NMR (D$_2$O) δ 7.55–7.37 (series of m, 2H), 7.29–7.15 (m, 1H), 7.07–6.96 (m, 1H), 6.70–6.60 (m, 1H), 4.38 (m, 1H), 3.80–3.58 (m, 3H), 3.38 (br s, 1H), 3.19–2.75 (series of m, 2H), 2.52–2.41 (m, 1H), 2.11–2.03 (m, 1H), 1.86–0.79 (series of m, 7H); 13C NMR (D$_2$O) ppm 176.53, 176.23, 176.15, 175.72, 175.57, 175.43, 165.51, 163.92, 160.29, 159.19, 158.14, 137.88, 137.75, 131.18, 131.06, 129.30, 129.20, 126.84, 124.13, 123.85, 122.35, 114.03, 109.10, 107.45, 92.48, 92.26, 78.37, 75.26, 74.65, 63.93, 63.74, 63.32, 58.78, 55.95, 52.87, 51.53, 51.36, 51.12, 50.77, 45.25, 42.64, 42.35, 41.79, 34.67, 31.22, 30.28, 29.13, 27.84, 27.68, 26.89, 26.40, 25.86, 25.07, 24.64, 24.46, 24.06, 22.94, 22.75; IR (KBr, cm$^{-1}$) 3500–3000, 2956, 2876, 1662, 1598, 1526, 1438, 1346, 748; MS m/z (MH$^+$—HCl) calcd 399.2145, obsd 399.2140.

Anal. Calcd for $C_{20}H_{26}N_6O_3 \cdot 1.0HCl \cdot 0.70H_2O$: C, 53.68; H, 6.40; N, 18.78; $H_2O$, 2.82.

Found: C, 52.49; H, 6.24; N, 16.79; $H_2O$, 2.72.

EXAMPLE 12

$N^\alpha$-[N-Phenylacetyl-L-prolyl]-L-arginine aldehyde Hydrochloride

A:
$N^\alpha$-[N-Phenylacetyl-L-prolyl]-$N^\delta$-benzyloxycarbonyl-L-arginine lactam Obtained 3.45 g (45%), white foam, m.p. 62°–70° C.; 1H ZNMR ( $CD_3SOCD_3$ ) δ 9.56 (br s, 0.5H), 9.14 (br s, 0.5H), 8.52 and 8.17 (2d, J=8.1, 8.0 Hz, 1H), 7.36–7.16 (m, 10H), 5.04 (m, 2H), 4.61–4.15 ( 3m, 3H), 3.73–3.38 (m, 5H), 2.24–1.59 (series of m, 8H); $^{13}$C NMR ($CD_3SOCD_3$) ppm 175.57, 175.35, 172.04, 171.90, 169.39, 168.89, 162.88, 159.72, 15 9.53, 137.11, 135.64, 135.60, 129.71, 129.66, 12 9.47, 129.32, 128.44, 128.24, 128.13, 128.05, 12 7.88, 126.35, 66.15, 60.02, 59.85, 59.64, 59.28, 50.7 8, 50.34, 47.25, 46.71, 43.25, 43.01, 42.22, 31.8 8, 29.56, 25.12, 24.56, 24.31, 22.34, 20.85, 20.0 4, 19.85, 14.17; IR (KBr, cm$^{-1}$) 3372, 2950, 1684, 1640, 1612, 1498, 1266, 1180, 1158, 1104, 750, 698; MS m/z (MH ®) calcd 506.2403, obsd 506.2382.

Anal. Calcd for $C_{27}H_{32}N_5O_5 \cdot 0.19H_2O$: C, 63.72; H, 6.22; N, 13.76; $H_2O$, 0.67.

Found: C, 63.61; H, 6.17; N, 13.41; $H_2O$, 0.68.

B:
$N^\alpha$-[N-Phenylacetyl-L-prolyl]-$N^\delta$-benzyloxycarbonyl-L-arginine aldehyde Obtained 1.65 g (64%), white foam, m.p. 78°–85° C.; $^1$H NMR ($CD_3SOCD_3$) δ 8.07–7.94 (br m, 2H), 7.78 and 7.63 (2d, J=7.9, 8.5 Hz, 1H), 7.40–7.14 (m, 10H), 6.19–5.75 (series of m, 2H), 5.03–4.90 (m, 2H), 4.60–4.48 and 4.39–4.37 (2m, 1H), 3.80–3.16 (series of m, 6H), 3.08–2.95 (m, 1H), 2.17–1.65 (series of m, 6H), 1.49–1.39 (m, 2H); $^{13}$C NMR ($CD_3SOCD_3$) ppm 171.54, 171.41, 170.87, 169.10, 169.03, 168.74, 163.32, 161.16, 160.52, 137.99, 137.90, 135.76, 135.64, 135.60, 129.57–126.36 (13 lines, olefinic), 74.47, 73.76, 65.50, 65.42, 59.56, 59.14, 58.91, 49.16, 48.98, 47.26, 46.73, 31.92, 29.45, 29.29, 24.42, 24.17, 23.86, 22.46, 19.40;

IR (KBr, cm$^{-1}$) 3362, 2946, 2876, 1616, 1522, 1454, 1282, 1082, 996, 698; MS m/z (MH$^+$) calcd 508.2560, obsd 508.2544.

Anal. Calcd for $C_{27}H_{33}N_5O_5 \cdot 0.04MeOH \cdot 0.40H_2O$: C, 62.38; H, 6.77; N, 13.28; $H_2O$, 1.37.

Found: C, 62.02; H, 6.38; N, 13.33; $H_2O$, 1.46.

C: $N^\alpha$-[N-phenylacetyl-L-prolyl]-L-arginine aldehyde Hydrochloride

Obtained 810.1 mg (100%), white solid, m.p. 108°–115° C. (sealed tube); $^1$H NMR ($D_2O$) δ 7.43–7.33 (m, 3H), 7.30–7.12 (m, 2H), 5.41–5.31 and 5.03–4.87 (2m, 1H), 4.64–4.63 and 4.45–4.35 ( 2m, 1H), 4.02–3.48 (series of m, 5H), 3.28–3.09 (2m, 2H), 2.30–2.25 (m, 1H), 2.07–1.49 (series of m, 8H); $^{13}$C NMR ($D_2O$) ppm 176.65, 176.29, 175.95 175.56, 175.23, 175.07, 174.97, 159.68, 159.29, 158.56, 136.48, 136.43, 136.39, 136.18, 131.31, 131.25, 131.05, 130.84, 129.27, 129.16, 92.48, 79.37, 78.44, 63.16, 62.97, 62.71, 62.64, 62.52, 62.42, 56.18, 55.84, 51.68, 51.44, 50.37, 50.11, 49.63, 42.87, 42.83, 42.77, 42.17, 41.93, 34.02, 32.03, 31.88, 31.79, 29.39, 27.62, 26.96, 26.49, 26.43, 26.36, 24.83, 24.65, 23.31, 20.65; (KBr, cm$^{-1}$) 3500–3000, 2952, 1658, 1540, 1446, 1302, 1202, 1000, 718, 698; MS m/z (MH$^+$—HCl) calcd 374.2192, obsd 374. 2176.

Anal. Calcd for $C_{19}H_{27}N_5O_3 \cdot 1.0HCl \cdot 0.70H_2O$: C, 52.04; H, 7.02; N, 16.58; $H_2O$, 2.99.

Found: C, 54.19; H, 7.06; N, 16.24; $H_2O$, 2.92.

EXAMPLE 13

$N^\alpha$-[N-(3-Cyclohexylpropanoyl)-L-prolyl]-L-arginine aldehyde Hydrochloride A: $N^\alpha$[N-(3-Cyclohexylpropanoyl)-L-prolyl]-$N^\delta$-benzyloxycarbonyl-L-arginine lactam Isobutyl chloroformate (1.50 mL, 11.79 mmol) was added dropwise to a cold (−20° C.) solution of 3-cyclohexylpropanoic acid (1.84 g, 11.79 mmol) and N-methylmorpholine (1.30 mL, 11.79 mmol) in dry dimethylformamide (20 mL). After about 30 minutes at about −20° C., the mixture was canulated into a cold (−20° C.) suspension of $N^\alpha$-L-prolyl-$N^\delta$-benzyloxycarbonyl-L-arginine lactam dihydrochloride (5.00 g, 11.79 mmol) and triethylamine (1.64 mL, 11.79 mmol) in dry dimethylformamide (125 mL). The mixture was stirred at about −20° C. for about 30 minutes before it was gradually warmed to room temperature over the course of about 3 hours. Following evaporation of the solvent in vacuo, the residue was taken up in benzene and washed with saturated sodium bicarbonate solution, saturated citric acid solution and brine prior to drying and solvent concentration. The residue was purified by column chromatography on silica gel (elution with 90% ethyl acetate in hexanes) and furnished 2.60 g (42%) of the title compound as a white foam, m.p. 58°–68° C.; $^1$H NMR ($CD_3SOCD_3$) δ 9.56 (br s, 1H), 9.14 (br s, 1H), 8.40 and 8.12 (2d, J=8.2 Hz, 8.2 Hz, 1H), 7.38–7.26 (m, 6H), 5.03 (s, 2H), 4.58–4.47 (m, 1H), 4.38–4.29 (m, 2H), 4.19–4.12 (m, 1H), 3.72–3.27 (series of m, 3H), 2.26–1.61 (series of m, 17H), 1.39–1.32 (m, 2H), 1.18–1.13 (m, 5H), 1.01–0.79 (m, 2H); —C NMR ($CD_3SOCD_3$) ppm 175.54, 175.32, 172.16, 172.04, 171.79, 171.43, 171.04, 162.88, 162.84, 159.70, 159.56, 137.11, 128.43, 128.03, 127.87, 66.14, 59.82, 59.09, 50.62, 50.39 46.82, 46.45, 43.10, 42.34, 36.79, 32.81, 32.74, 31.83 31.29, 30.96, 29.45, 26.45, 26.23, 25.89, 25.11 24.67, 24.26, 22.34, 19.98, 19.88; IR (KBr, cm$^{-1}$) 3372, 2924, 1688, 1612, 1510, 1448, 1266, 1180, 1158, 1104; MS m/z (MH$^+$) calcd 526.3029, obsd 526.3012.

Anal. Calcd for $C_{28}H_{39}N_5O_5 \cdot 0.15H_2O$: C, 63.66; H, 7.50; N, 13.26; $H_2O$, 0.51.

Found: C, 63.55; H, 7.50; N, 12.88; $H_2O$, 0.52.

B:
$N^\alpha$-[N-(3-cyclohexylpropanoyl)-L-prolyl]-$N^\delta$-benzyloxycarbonyl-L-arginine aldehyde Obtained 2.75 g (57%), white foam, m.p. 74–81° C.; NMR ($CD_3SOCD_3$) δ0 8.10–7.93 (m, 1H), 7.74 and 7.56 (2d, J=7.9 and 8.5 Hz, 0.5H), 7.36–7.24 (m, 5H), 5.86–5.74 (m, 1H), 5.02–4.91 (m, 2H), 4.44–4.33 (2m, 1H), 3.85(m, 3.20 (series of m, 4H), 3.13–2.99 (m, 1H), 2.25–2.20 (m, 1H), 2.18–1.27 (series of m, 16H), 1.18–1.12 (m, 4H), 0.89–0.66 (m, 2H); $^{13}$C NMR (CD₃SOCD₃) ppm 172.26, 172.04, 171.71, 171.60, 171.28, 171.13, 171.03, 170.93, 163.35, 161.23, 160.55, 138.02, 137.94, 128.35–126.51 (9 lines, olefinic), 74.53, 73.80, 65.52, 65.46, 63.01, 59.21, 50.99, 58.74, 48.98, 47.38, 47.24, 46.90, 46.54, 37.26, 36.92, 36.81, 32.83, 32.76, 32.67, 32.02, 31.90, 31.38, 31.02, 29.31, 29.10, 26.26, 25.91, 24.42, 24.26, 23.91, 22.54, 22.32, 21.30, 19.43; IR (KBr, cm$^{-1}$) 3364, 2924, 2852, 1616, 1524, 1448, 1282, 1084, 996; MS m/z (MH+) calcd 528.3186, obsd 528.3178.

Anal. Calcd for $C_{28}H_{41}N_5O_5 \cdot 0.40H_2O$: C, 62.88; H, 7.88; N, 13.10; $H_2O$, 1.35.

Found: C, 62.30; H, 7.80; N, 12.51; $H_2O$, 1.09.

C: N$^\alpha$-[N-(3-Cyclohexylpropanoyl)-L-prolyl]-L-arginine aldehyde Hydrochloride Obtained 837.1 mg (95), white foam, m.p. 119°–127° C. (sealed tube); ¹H NMR (D₂O) 6 5.49–5.35 (m, 1H), 5.02–4.92 (m, 1H), 4.60–4.57 and 4.46–4.37 (2m, 1H), 4.06–3.82 (3m, 1H), 3.67–3.46 (m, 3H), 3.35–3.22 (m, 1H), 2.44–2.39 (m, 2H), 2.31–1.56 (series of m, 16H), 1.52–1.47 (m, 2H), 1.25–1.19 (m, 4H), 0.97–0.86 2H); ¹³C NMR (D₂O) ppm 177.81, 177.56, 176.76, 176.67, 176.00, 175.94, 159.35, 158.67, 95.01, 92.49, 92.40, 78.50, 62.69, 62.44, 62.23, 62.05, 55.82, 51.65, 51.42, 50.11, 49.35, 52.85, 42.20, 41.96, 38.97, 34.69, 34.54, 34.49, 34.19, 33.94, 33.88, 33.82, 31.83, 28.29, 27.96, 27.64, 27.01, 26.47, 24.90, 24.75, 24.46, 23.43; IR (KBr, cm$^{-1}$) 3326–3000, 2924, 2850, 1658, 1624, 1540, 1448; MS m/z (MH+ −HCl) calcd 394.2818, obsd 394.2814.

Anal. Calcd for $C_{30}H_{35}N_5O_3 \cdot 1.0HCl \cdot 0.30H_2O$: C, 55.18; H, 8.48; N, 16.09; $H_2O$, 1.24.

Found: C, 55.37; H, 8.25; N, 15.85; $H_2O$, 0.85.

EXAMPLE 14

N$^\alpha$-[N-(3-Phenylpropanoyl)-L-prolyl]-L-arginine aldehyde Hydrochloride

A: N$^\alpha$-[N-(3-Phenylpropanoyl)-L-prolyl]-N$^\delta$-benzyloxycarbonyl-L-arginine lactam White foam, m.p. 45°–52° C.; ¹H NMR (CDCl₃) 9.60–9.36 (br s, 1H), 7.79–7.77, 7.67–7.65 (d, 1H), 7.39–7.14 (m, 10H), 5.11 (s, 2H), 4.83–4.75 (m, 1H), 4.64–4.50 (m, 2H), 3.60–3.40 (m, 2H), 3.38–3.25 (m, 1H), 3.01–2.94 (m, 2H), 2.66–2.59 (m, 2H), 2.42–2.32 (m, 2H), 1.94–1.74 (m, 6H), 1.53–1.42 (m, 1H); ¹³C NMR (CDCl₃) ppm 175.48, 172.60, 171.39, 163.66, 160.11, 140.97, 136.67, 128.48, 128.42, 128.23, 127.96, 126.22, 67.14, 59.77, 51.21, 47.55, 41.56, 36.39, 31.89, 27.31, 24.92, 24.82, 19.74; IR (KBr, cm$^{-1}$) 3360, 2940, 1680, 640, 1610, 1490, 1450, 1260; MS m/z (MH+) 520.

Anal. Calcd for $C_{28}H_{35}N_5O_5 \cdot 1.0H_2O$: C, 63.62; H, 6.48; N, 13.25.

Found: C, 63.22; H, 6.75; N, 12.87.

N$^\alpha$-[N-(3-Phenylpropanoyl)-L-prolyl]-N$^\delta$-benzyloxycarbonyl-L-arginine aldehyde White foam, m.p. 57°–67° C.; ¹H NMR (CDCl₃) 9.81, 9.47, 8.96, 9.20 (br m, 1H), 7.68–7.15 (m, 10H), 5.20–5.00 (br s, 2H), 4.45–4.33 (br m, 1H), 3.50–3.27 (m, 5H), 2.96–2.50 (m, 7H), 1.99–1.71 (m, 8H); IR (KBr, cm$^{-1}$) 3300, 2950, 1740, 1680, 1630, 1520, 1450, 1240; MS m/z (MH+) 522.

C: N$^\alpha$-[N-(3-Phenylpropanoyl)-L-prolyl]-L-arginine aldehyde Hydrochloride White foam, m.p. 68°–80° C.; ¹H NMR (D₂O) 7.40–7.27 (m, 5H) 4.3 (br s, 1H), 4.13–3.16 (m, 5H), 2.91 (br s, 3H), 2.72 (br s, 2H), 2.18–1.20 (m, 8H); ¹³C NMR (D₂O) ppm 176.74, 176.38, 176.30, 176.24, 159.34, 158.70, 142.80, 130.69, 130.38, 128.42, 105.87, 72.46, 78.50, 65.88, 63.69, 62.62, 62.35, 26.24, 55.77, 51.39, 50.14, 48.27, 42.58, 41.90, 37.59, 37.51, 33.77, 32.74, 32.36, 31.77, 27.54, 26.28, 24.78, 24.44, 19.17, 15.22; IR (film on NaCl, cm$^{-1}$) 3320, 2950, 1660, 1630, 1450, MS m/z (MH+ −HCl) 388.

Anal. Calcd for $C_{20}H_{29}N_5O_3 \cdot 1.0HCl \cdot H_2O$: C, 52.85; H, 7.35; N, 15.41.

Found: C, 53.35; H, 7.40; N, 14.63.

EXAMPLE 15

A: N$^\alpha$-[N-Phenoxyacetal-L-prolyl]-N$^\delta$-benzyloxycarbonyl-L-arginine lactam Off-white foam, m.p. 145°–146° C.; ¹H NMR (CDCl₃) 9.65 (br s, 1H), 9.35 (br s, 1H), 7.49–7.21 (m, 8H), 7.04–6.85 (m, 4H), 5.11 (s, 2H), 4.62 (s, 2H), 4.84–4.52 (m, 3H), 3.68–3.38 (m, 3H), 2.33–1.77 (m, 6H), 1.50–1.20 (m, 1H); ¹³C NMR (CDCl₃) ppm 175.33, 175.27, 175.12, 170.93, 170.82, 168.25, 165.65, 162.60, 160.11, 157.79, 136.67, 129.60, 128.60, 128.44, 128.25, 127.99, 121.71, 114.61, 67.40, 67.15, 60.24, 60.04, 51.19, 51.04, 47.55, 46.77, 41.66, 41.58, 36.50, 31.43, 27.23, 25.10, 24.72, 24.47, 19.76; IR (KBr, cm$^{-1}$) 3280, 3080, 2940, 1790, 1660, 1600, 1500, MS m/z (MH+) 522.

Anal. Calcd for $C_{27}H_{31}N_5O_6 \cdot 1.0H_2O$: C, 60.10; H, 6.16; N, 12.98

Found: C, 60.25; H, 6.04; N, 12.94.

B: N$^\alpha$-[N-Phenoxyacetyl-L-prolyl]-N$^\delta$-benzyloxycarbonyl-L-arginine aldehyde Off-white foam, m.p. 65°–78° C.; ¹H NMR (CDCl₃) 7.35–7.22 (m, 7H), 6.96–6.70 (m, 3H), 5.68–5.50 (br s, 1H), 5.11 (s, 2H), 4.59 (s, 2H), 4.63–4.57 (m, 1H), 4.08–4.02 (br s, 1H), 3.59–3.41 (m, 2H), 2.13–1.80 (m, 5H), 1.63–1.39 (m, 4H); ¹³C NMR (CDCl₃) ppm 168.38, 164.11, 162.03, 157.94, 137.49, 129.88, 128.56, 128.25, 127.95, 121.95, 114.77, 67.45, 66.85, 60.84, 46.94, 29.44, 25.27; IR (KBr, cm$^{-1}$) 3350, 2940, 1650, 1590, 1520, 1490, 1270; MS m/z (MH+) 524.

Anal. Calcd for $C_{27}H_{33}N_5O_6 \cdot 1.0H_2O$: C, 59.88; H, 6.51; N, 12.98.

Found: C, 59.47; H, 6.16; N, 12.06.

C: N$^\alpha$-[N-Phenoxyacetyl-L-prolyl]-L-arginine aldehyde Hydrochloride

Off-white foam, m.p. 95°–105° C. (dec.); ¹H NMR (D₂O) 7.38–7.33 (m, 2H), 7.07–6.90 (m, 3H), 5.43 (m, 1H), 4.86 (s, 2H), 4.49–4.41 (m, 1H), 3.90–3.85 (m, 1H), 3.60–3.47 (m, 3H), 3.21–2.83 (m, 1H), 2.37–1.42 (m, 8H); IR (KBr, cm$^{-1}$) 3350, 1660, 1495, 1230; MS m/z (MH+) 390.

EXAMPLE 16

N$^\alpha$-[Glycl-D-phenylalanyl-L-prolyl]-L-arginine aldehyde Dihydrochloride

A:
N$^\alpha$-[Benzyloxycarbonyl-glycyl-D-phenylalanyl-L-prolyl]-N$^\delta$-benzyloxycarbonyl-L-arginine lactam Obtained 3.69 g (47%), white foam, m.p. 87°–93° C.; $^1$H NMR (CD$_{SOCD3}$) δ 9.57 (br s, 1H), 9.17 (br s, 1H), 8.59–8.44 (2m, 1H), 8.29–8.05 (2m, 1H), 7.46–7.20 (m, 15H), 5.07–5.01 (m, 4H), 4.97–4.95 (m, 1H), 4.75–4.70 (m, 1H), 4.59–4.49 (m, 1H), 4.40–4.28 (m, 2H), 3.94–3.38 (series of m, 4H), 3.04–2.79 (m, 3H), 2.26–2.21 (m, 1H), 2.00–1.74 (series of m, 12H); —C NMR (CD$_3$SOCD$_3$) ppm 175.30, 172,31, 171.75, 171.35, 170.59, 169.34, 169.07, 168.89, 162.89, 159.58, 159.55, 158.06, 156.50, 138.34, 137.11, 137.05, 129.38, 129.20, 128.43, 128.26, 128.14, 128.04, 127.87, 127.80, 127.76, 126.68, 126.34, 66.15, 65.50, 59.85, 59.39, 52.39, 52.17, 50.45, 46.65, 43.22, 43.00, 42.47, 42.34, 37.77, 31.99, 29.18, 24.58, 23.95, 22.26, 19.89, 14.17; IR (KBr, cm$^{-1}$) 3364, 2952, 1682, 1648, 1612, 1512, 1512, 1512, 1454, 1264, 1178, 1158, 1104, 700; MS m/z (MH$^+$) calcd 726.3251, obsd 726.3236.

Anal. Calcd for C$_{38}$H$_{43}$N$_7$O$_8$.018EtOAc.0.26H$_2$O: C, 62.33; H, 6.05; N, 13.15; H$_2$O, 0.63.

Found: C, 61.92; H, 5.96; N, 13.31; H$_2$O, 0.64.

B:
N$^\alpha$-[Benzyloxycarbonyl-glycyl-D-phenylalanyl-L-prolyl]-N$^\delta$-benzyloxycarbonyl-L-arginine aldehyde Obtained 1.99 g (67%), white foam, m.p. 96°–116° C.; $^1$H NMR (CD$_3$SOCD$_3$) δ 8.34–8.24 (m, 1H), 8.16–8.11 and 7.78–7.76 (2m, 1H), 7.41–7.02 (m, 15H), 6.06–5.72 (series of m, 1H), 4.99–4.82 (m,4H), 4.73–4.61 (m, 1H), 4.26–4.22 (m, 1H), 3.77–3.31 (series of m, 3H), 3.17–2.67 (m, 1H), 1.95 (m, 1H), 1.74 (m, 3H), 1.55 (m, 1H), 1.42–1.39 (m, 2H); $^{13}$C NMR (CD$_3$SOCD$_3$) ppm 171.98, 171.36, 171.08, 170.43, 170.31, 169.63, 169.21, 169.01, 168.48, 163.31, 161.18, 160.93, 160.57, 156.45, 138.34, 137.99, 137.86, 137.09, 136.99, 129.34–126.30 (13 lines, olefinic), 90.65, 73.63, 65.52, 65.45, 65.37, 59.83, 59.44, 52.59, 49.53, 49.08, 47.61, 46.65, 43.14, 42.92, 37.23, 36.56, 32.26, 29.04, 23.98, 22.27, 20.82, 19.34, 14.15, IR (KBr, cm$^{-1}$) 3386, 2948, 2880, 1648, 1524, 1454, 1278, 1082, 700; MS m/z (MH$^+$) calcd 728.3408, obsd 728.3386.

Anal. Calcd for C$_{38}$H$_{45}$N$_7$O$_8$.0.34H$_2$O: C, 62.19; H, 6.28; N, 13.36; H$_2$O, 0.84.

Found: C, 62.17; H, 6.37; N, 13.06; H$_2$O, 0.83.

C: N$^\alpha$-[Glycyl-D-phenylalanyl-L-prolyl]-L-arginine aldehyde Dihydrochloride

Obtained 730.0 mg (100%), dense, off-white solid, m.p. 161°–181° C. (closed tube); $^1$H NMR (D$_2$O) δ 7.40–7.32 (m, 3H), 7.28–7.19 (m, 2H), 5.40–5.35 (m, 1H), 5.02–4.87 (m, 1H), 4.40–4.22 (m, 1H), 3.99–3.43 (series of m, 2H), 3.30–3.19 (m, 1H), 3.09–2.90 (2m, 3H), 2.11–1.97 (m, 1H), 1.84–1.48 (series of m, 6H); $^{13}$C NMR (D$_2$O) ppm 175.99, 175.85, 175.36, 173.85, 173.50, 173.05, 168.50, 168.23, 137.74, 137.55, 131.32, 130.82, 129.50, 129.24, 92.35, 79.19, 78.45, 78.23, 62.79, 62.60, 62.28, 55.97, 55.31, 55.02, 51.43, 50.20, 49.82, 42.78, 42.25, 42.13, 41.91, 39.14, 38.94, 31.45, 27.14, 26.58, 26.21, 25.99, 24.80, 24.63, 23.43; IR (KBr, cm$^{-1}$) 3500–2800, 1652, 1548, 1452, 1260, 704; MS m/z (MH$^+$—2HCL) calcd 460.2672, obsd 460.2682.

Anal. Calcd for C$_{22}$H$_{33}$N$_7$O$_4$.2HCl.0.7H$_2$O: C, 48.48; H, 6.74; N, 17.99; H$_2$O, 2.31.

Found: C, 48.78; H, 6.75; N, 17.61; H$_2$O, 2.09.

EXAMPLE 17

A:
N-[2-[2-Amino-4-phenyl-5-thiazolyl]acetyl-L-prolyl]-N$^\delta$-benzyloxycarbonyl-L-arginine aldehyde

A:
N-[2-[2-Amino-4-phenyl-5-thiazolyl]acetyl-L-proline tert-butyl ester

Obtained 12.15 g (73%), yellow foam, m.p. 45°–50° C.; $^1$H NMR (CDCl$_3$) δ 7.46–7.41 (m, 2H), 7.35–7.23 (m, 3H), 5.51 (s, 2H), 4.34–4.30 and 4.07–4.03 (2m, 1H), 3.71–3.20 (series of m, 4H), 2.11–1.75 (m, 4H), 1.39 and 1.28 (2s, 9H); $^{13}$C NMR (CDCl$_3$) ppm 171.18, 170.78, 168.85, 168.43, 166.57, 166.50, 162.45, 147.95, 147.89, 134.93, 134.87, 128.46, 128.23, 127.46, 114.86, 82.10, 81.16, 59.86, 59.67, 46.94, 46.56, 36.37, 33.12, 31.25, 29.03, 27.82, 27.62, 24.51, 22.70; IR (KBr, cm$^{-1}$) 3312, 3146, 2976, 2932, 1736, 1650, 1532, 1444, 1428, 1392, 1368, 1292, 1152, 776, 702; MS m/z (MH$^+$) calcd 388.1695, obsd 388.1699.

Anal. Calcd for C$_{20}$H$_{25}$N$_3$O$_3$S.0.5DMF.0.3H$_2$O: C, 60.14; H, 6.84; N, 11.42; H$_2$O, 1.26.

Found: C, 60.45; H, 6.68; N, 11.11; H$_2$O, 1.41.

B:
N-[2-[2-Amino-4-phenyl-5-thiazolyl]acetyl]-L-proline Hydrochloride

Obtained 10.45 g (71%), off-white solid, m.p. 78°–88° C. (closed tube); $^1$H NMR(D$_2$O) δ 7.41–7.39 (m, 3H), 7.29–7.21 (m, 2H), 4.35–4.26 (m, 1H), 3.66 (s, 1H), 3.43–3.34 (m, 2H), 2.20–2.13 (m, 1H), 1.92–1.80 (m, 2H); —C NMR (D$_2$O) ppm 178.49, 172.13, 171.77, 138.55, 132.96, 131.90, 130.94, 130.08, 115.08, 62.13, 50.32, 34.19, 31.77, 26.98; IR (KBr, cm$^{-1}$) 3600–2500, 1738, 1626, 1452, 1406, 1254, 1188, 1120, 872, 774, 700; MS m/z (MH$^+$—HCl) calcd 332.1069, obsd. 332.1071.

Anal. Calcd. for C$_{16}$H$_{17}$N$_3$O$_3$S.1.0HCl.1.0Dioxane.1.0 H$_2$O: C, 50.68; H, 5.96; N, 8.87; H$_2$O, 3.80.

Found: C, 50.98; H, 6.04; N, 9.05; H$_2$O, 3.80.

C:
N$^\alpha$-[2-[2-Amino-4-phenyl-5-thiazolyl]acetyl-L-prolyl]-N$^\delta$-benzyloxycarbonyl-L-arginine lactam Obtained 3.31 g (40%), white foam, m.p. 108°–118° C.; $^1$H NMR (CD$_3$SOCD$_3$) δ 9.56 (br s, 1H), 9.14 (br s, 1H), 8.39 and 8.19 (2d, J =8.0 Hz, 1H), 7.52–7.50 (m, 1H), 7.45–7.24 (m, 9H), 6.85–6.83 (m, 2H), 5.04 (s, 2H), 4.60–4.16 (series of m, 3H), 3.77–3.35 (series of m, 6H), 2.05–1.37 (series of m, 10H); $^{13}$C NMR (CD$_3$SOCD$_3$) ppm 177.18, 176.86, 173.42, 173.39, 173.16, 170.15, 169.78, 168.13, 167.97, 164.53, 161.27, 161.21, 138.76, 137.05, 130.09, 129.90, 129.79, 129.69, 129.53, 128.84, 18.72, 114.76, 114.72, 67.81, 61.51, 61.40, 61.10, 52.31, 52.06, 48.71, 48.57, 44.55, 43.96, 34.30, 34.11, 33.52, 31.17, 26.29, 25.94, 24.01, 22.50, 21.54, 15.82; IR (KBr, cm$^{-1}$) 3362, 3204, 2950, 1684, 1640, 1612, 1526, 1444, 1376, 1294, 1264, 1178, 1158, 700; MS m/z (MH$^+$) calcd 604.2342, obsd 604.2347.

Anal. Calcd for C$_{30}$H$_{33}$N$_7$O$_5$S.0.25EtOAc.0.5H$_2$O: C, 58.66; H, 5.72; N, 15.45; H$_2$O, 1.42.

Found: C, 58.80; H, 5.60; N, 15.44; H$_2$O, 2.78.

D:

N$^\alpha$-[2-[2-Amino-4phenyl-5-thiazolyl]acetyl-L-prolyl]-N$^\delta$-benzyloxycarbonyl-L-arginine aldehyde Obtained 1.86 g (62%) white solid, m.p. 238°–245° C. (dec.); $^1$H NMR (CD$_3$SOCD$_3$) δ 8.01–7.69 (m, 1H), 7.51–7.45 (m, 2H), 7.39–7.25 (m, 8H), 6.91 (br s, 2H), 6.33–5.57 (series of m, 1H), 5.04–4.94 (m, 2H), 4.48–4.33 (m, 2H), 3.97–3.57 (m, 2H), 3.56–3.23 (m, 4H), 1.99–1.28 (series of m, 8H); $^{13}$C NMR (CD$_3$SOCD$_3$) ppm 175.04, 174.90, 174.14, 173.04, 172.73, 172.01, 171.69, 161.02, 157.57, 140.17–127.95 (16 lines, olefinic), 67.19, 67.09, 61.50, 61.22, 60.96, 56.00, 55.77, 54.22, 53.31, 48.28, 38.94, 37.87, 33.60, 30.58, 29.88, 29.64, 25.68, 23.85; IR (KBr, cm$^{-1}$) 3600–3100, 2952, 1632, 1526, 1446, 1294, 1242, 702; MS m/z (MH+) calcd for C$_{30}$H$_{35}$N$_7$O$_5$S: 606.2499, obsd 606.2480.

EXAMPLE 18

N$^\alpha$-[N-(Aminoiminomethyl)-D-phenylalanyl-L-prolyl]-L-arginine aldehyde Dihydrochloride A: D-Phenylalanyl-L-proline tert-Butyl ester Hydrochloride To a well-stirred, nitrogen-blanketed mixture of benzyloxycarbonyl-L-phenylalanyl-L-proline tert-butyl ester (23.00 g, 50.82 mmol) and 1[hydrochloric acid (51 mL, 51 mmol) in tetrahydrofuran (500 mL) was added 10% palladium on carbon (2.3 g). The suspension was stirred at ambient temperature for about 5 minutes before the nitrogen blanket was removed and replaced with hydrogen at one atmosphere. After about 5 hours, the suspension was suction-filtered through Celite and the filtrate was concentrated down to dryness to afford 19.17 g (100%) of the title compound as a dense, white solid, m.p. 168°–170° C.; $^1$H NMR (D$_2$O) δ 7.41–7.38 (m, 3H), 7.28–7.26 (m, 2H), 4.56–4.51 (m, 1H), 4.20–4.16 (m, 1H), 3.53–3.46 (m, 1H), 3.27–3.21 (m, 1H), 3.14–3.07 (m, 1H), 2.72–2.64 (m, 1H), 2.05–1.65 (m, 4H), 1.58–1.49 (m, 1H), 1.45 (s, 9H); $^{13}$C NMR (D$_2$O) ppm 174.85, 169.57, 135.40, 131.49, 131.10, 130.16, 86.09, 62.33, 54.82, 51.95, 49.51, 38.59, 30.63, 29.11, 25.88; IR (KBr, cm$^{-1}$) 3242, 2980, 2930, 2874, 1750, 1730, 1658, 1524, 1488, 1452, 1366, 1150; MS m/z (MH+ −HCl) calcd 319.2022, obsd 319.2013.

Anal. Calcd for C$_{18}$H$_{26}$N$_2$O$_3$.0.9HCl: C, 61.34; H, 7.74; N, 7.95; Cl, 9.06, H$_2$O, 0.36.

Found: C, 61.48; H, 7.61; N, 7.44; Cl, 9.09; H$_2$O, 0.33.

B:

N-(N,N'-Dibenzyloxycarbonylaminoiminomethyl)-D-phenylalanyl-L-proline and tert-Butyl Ester N,N'-Dicarbobenzyloxy-S-methylisothiourea (3.03 g, 8.45 mmol) was added in one portion to a well-stirred mixture of D-phenylalanyl-L-proline tert-butyl ester hydrochloride (3.00 g, 8.45 mmol) and triethylamine (1.2 mL, 8.45 mmol) in anhydrous tetrahydrofuran (30 mL). The mixture was refluxed for about 96 hours under nitrogen. Upon cooling, the solvent was removed in vacuo and the residue was partitioned between ethyl acetate and saturated sodium bicarbonate solution. The organic phase was then separated, washed with brine, dried, and concentrated. Purification of the residue by flash chromatography on silica gel (gradient elution with 15% ethyl acetate in hexanes followed by 25% ethyl acetate in hexanes) afforded 1.26 g (24%) of the tert-butyl ester as a white foam, m.p. 58°–64° C.; MS (m/z) MH+629.

The tert-butyl ester (1.20 g, 1.91 mmol) was then treated to a cold (0° C.), saturated solution of hydrogen chloride in ethyl acetate (200 mL). The mixture was stirred for about 3 hours before it was concentrated down in vacuo. There was isolated 677.4 mg (62%) of the acid as a white foam. The acid was carried on directly into the next reaction.

C:

N$^\alpha$-[N-(N,N'-Dibenzyloxycarbonylamimoiminomethyl)-D-phenylalanyl-L-prolyl]-N$^\delta$-benzyloxycarbonyl-L-arginine lactam Obtained 0.24 g (42%), white foam, m p 74°–84° C.$^1$H NMR (CDCl$_3$) δ 11.39 (m, 1H), 9.52 and 9.26 (2 brs, 1H), 8.67–8.65 (m, 1H), 7.36–7.09 (m, 20H), 5.17–5.06 (m, 4H), 4.93 (s, 2H), 4.73–4.57 (series of m, 2H), 4.46–4.17 (series of m, 2H), 3.95–3.91 (m, 1H), 3.32–3.26 (m, 1H), 3.11–2.96 (m, 2H), 2.54–2.52 (m, 1H), 2.19–1.98 (m, 2H), 1.90–1.53 (m, 3H); IR (KBr, cm$^{-1}$) 3064, 3032, 2952, 1734, 1682, 1644, 1616, 1560, 1498, 1454, 1432, 1380, 1264, 1204, 1180, 1106, 1054, 748, 698; MS m/z (MH+), calcd for C$_{45}$H$_{49}$N$_8$O$_9$: 845. 3623, obsd 845. 3614.

D:

N$^\alpha$-[N-(N,N'-Dibenzyloxycarbonylaminoiminomethyl)-D-phenylalanyl-L-prolyl]-N$^\delta$-benzyloxycarbonyl-L-arginine aldehyde Obtained 101.5 mg (50%), white solid, m.p. 90°–95° C.; $^1$H NMR (CD$_3$SOCD$_3$) δ 11.61–11.57 (m, 1H), 11.39–11.32 (m, 1H), 8.80–8.75 (m, 1H), 8.60–7.95 (series of m, 2H), 7.42–7.26 (m, 17H), 7.14 (m, 3H), 6.12–5.95 (m, 1H), 5.24–5.20 (m, 2H), 5.12–4.95 (m, 4H), 4.30 and 3.62 (2m, 2H), 3.37 (s, 4H), 3.05 (m, 3H), 2.11–1.26 (series of m, IR (KBr, cm$^{-1}$) 3414, 2950, 1736, 1 644, 1618, 1556, 1522, 1498, 1454, 1380, 1286, 1206, 1 136, 1106, 1056, 746, 698; MS m/z (MH+).

Anal. Calcd for C$_{45}$H$_{51}$N$_8$O$_9$: 847.3779.

Found: 847.3787.

E:

N$^\alpha$-[N-(Aminoiminomethyl)-D-phenylalanyl-L-prolyl]-L-arginine aldehyde Dihydrochloride Obtained 54.0 mg (97%), pale-yellow solid, 138°–198° C. (sealed tube); $^1$H NMR (D$_2$O) δ 7.37–7.30 (m, 3H),7.27–7.24 (m, 2H), 4.32 (m, 1H), 3.83 (m, 1H), 3.69 (m, 1H), 3.53 (m, 2H), 3.30 (m, 1H), 3.14–2.98 (m, 2.18 (m, 1H), 1.88–1.30 (series of m, 8H); IR (KBr, cm$^{-1}$) 3600–3000, 1644, 1454, 1350, 1248, 1200, 1156, 1080, 702; MS m/z (MH+ −2HCL), calcd for C$_{21}$H$_{33}$N$_8$O$_3$-2HCl: 445.2676, obsd 445. 2661.

EXAMPLE 19

N$^\alpha$-[D-Phenylalanyl-L-alanyl]-L-arginine aldehyde Sulfate

A:

N$^\alpha$-[Benzyloxycarbonyl-D-phenylalanyl-L-alanyl]-N$^\delta$-benzyloxycarbonyl-L-arginine lactam Obtained 4.20 g (31%), white solid, m.p. 204°–206° C.; $^1$H NMR (CD$_3$SOCD$_3$) δ 9.58 (br s, 1H), 9.14 (br s, 1H), 8.29 (d, J=7.9 Hz, 1H), 8.20 (d, J=8.1 Hz, 1H), 7.58 (d, J=8.3 Hz, 1H), 7.41–7.04 (m, 15H), 5.03 (s, 2h), 4.91 (s, 2H), 4.64–4.55 (m, 1H), 4.38–4.25, (m, 3H), 3.62–3.35 (m, 1H), 2.93 (dd, J=13.5, 4.8 Hz, 1H), 2.78–2.70 (m, 1H) 2.06–1.97 (m, 1H), 1.85–1.61 (m, 3H), 1.17 (d, J=7.0 Hz, 3H); $^{13}$C NMR (CD$_3$SOCD$_3$) ppm 175.21, 172.17, 171.12, 162.89, 159.55, 155.99, 137.96, 137.09, 137.04, 129.38, 128.44, 128.37, 128.07, 127.89, 127.76, 127.48, 126.34, 66.15, 65.30, 56.24, 50.38, 47.85, 42.40, 37.62, 24.66, 19.86, 18.49; IR (KBr, cm$^{-1}$) 3374, 3292, 2952, 1694, 1644, 1612, 1532, 1454, 1378, 1264, 1194, 1160, 750, 698; MS m/z (MH+) calcd 643.2880, obsd 643.2883.

Anal. Calcd for $C_{34}H_{39}N_6O_7$: C, 63.54; H, 5.96; N, 13.08.

Found: C, 63.52; H, 5.93; N, 12.99.

$N^\alpha$-[Benzyloxycarbonyl-D-phenylalanyl-L-alanyl]-$N^\delta$-benzyloxycarbonyl-L-arginine aldehyde Obtained 0.87 g (52%), white foam, m.p. 118°-128° C.; $^1$H NMR (CD$_3$SOCD$_3$) δ 8.29-8.09 (m, 1H), 7.89-7.49 (series of m, 2H), 7.35-7.17 (m, 15H), 6.00-5.78 (m, 2H), 4.96-4.91 (m, 4H), 4.50-4.22 (m, 2H), 3.85 and 3.62 (2m, 2H), 3.35 (s, 2H), 3.18-2.89 (m, 2H), 2.76-2.68 (m, 1H), 1.72-1.64 (m, 1H), 1.52-1.37 (m, 2H), 1.21-1.03 (m, 3H); $^{13}$C NMR (CD$_3$SOCD$_3$) ppm 171.92, 171.30, 171.09, 163.34, 160.50, 155.94, 138.01, 137.89, 137.09, 129.36, 128.56, 128.36, 128.31, 128.09, 127.99, 127.76, 127.62, 127.57, 127.50, 126.32, 73.67, 65.47, 65.35, 56.27, 49.07, 47.84, 37.60, 37.19, 24.01, 23.88, 18.81, 18.56; IR (KBr, cm$^{-1}$) 3304, 3064, 3032, 2942, 1644, 1606, 1526, 1454, 1284, 1084, 744, 698; MS m/z (MH+) calcd 645.3037, obsd 645.3038.

Anal. Calcd for $C_{34}H_{40}N_6O_7 \cdot 0.50H_2O$: C, 62.47; H, 6.33; N, 12.86; H$_2$O, 1.38.

Found: C, 62.53; H, 6.23; N, 12.42; H$_2$O, 1.37.

C: $N^\delta$[D-Phenylalanyl-L-alanyl]-L-arginine aldehyde Sulfate

Obtained 510.4 mg (88%), white solid, m.p. 203°-223° C. (sealed tube); $^1$H NMR (D$_2$O) δ 7.37-7.35 (m, 3H), 7.24-7.22 (m, 2H), 4.27-3.75 (series of m, 3H), 3.60-3.04 (series of m, 4H), 1.82-1.35 (m, 4H), 1.11-0.83 (series of m, 3H); 1]C NMR (D$_2$O) ppm 170.94, 158.63, 135.77, 131.34, 131.04, 130.46, 129.94, 92.28, 78.30, 56.37, 55.98, 51.60, 42.59, 42.37, 41.81, 38.84, 27.46, 26.34, 24.73, 24.45, 18.60, 18.52; IR (KBr, cm$^{-1}$) 3600-2900, 1662, 1542, 1456, 1116, 702, 618; MS m/z (MH+−$H_2$SO$_4$), calcd for $C_{18}H_{29}N_6O_3 \cdot H_2SO_4$: 377.2301, obsd 377.2307.

EXAMPLE 20

$N^\alpha$-[(N-5-Dimethylamino-1-naphthalenesulfonyl)-glycyl-L-prolyl]-L-arginine aldehyde Hydrochloride A: Benzyloxycarbonyl-glycyl-L-proline tert-butyl ester Obtained 47.14 g (100%), crude, colorless oil; 1H NMR (CDCl$_3$) δ 7.32-7.23 (m, 5H), 5.75 (s, 1H), 5.08 (s, 2H), 4.39-3.88 (series of m, 3H), 3.73-3.36 (series of m, 2H), 2.20-1.84 (series of m, 4H), 1.48 and 1.44 (2s, 9H); $^{13}$C NMR (CDCl$_3$) ppm 171.18, 170.81, 167.38, 166.92, 15 6.42, 136.69, 128.67, 128.22, 128.13, 82.88, 81.75, 66.97, 59.88, 59.44, 46.87, 46.07, 43.55, 43.33, 31.60, 29.22, 28.14, 24.67, 22.37; IR (KBr, cm$^{-1}$) 3410, 3328, 2978, 2880, 1730, 1658, 1514, 1454, 1440, 1368, 1248, 1226, 1154, 1058, 1044, 752, 698; MS m/z (MH+) calcd 363.1920, obsd 363.1912.

Anal. Calcd for $C_{19}H_{26}N_2O_5$: C, 62.49; H, 7.36; N, 7.67.

Found: C, 62.58; H, 7.37; N, 7.58.

B: Glycyl-L-proline tert-butyl ester Hydrochloride

Obtained 2.69 g (100%), off-white solid, m.p. 143°-154° C. (closed tube); $^1$H NMR 9D$_2$O) δ 4.37-4.33 (m, 1H), 3.98-3.93 (m, 2H), 3.57-3.46 (m, 2H), 2.29-2.17 (m, 1H), 2.02 -1.92 (m, 3H), 1.44 and 1.42 (2s, 9H); $^{13}$C NMR (D$_2$) ppm 175.89, 175.09, 168.48, 168.09, 87.63, 86.81, 65,28, 63.08, 62.72, 49.76, 49.39, 43.06, 33.49, 31.63, 29.85, 26.88, 24.50; IR (KBr, cm$^{-1}$) 3432, 2982, 2882, 1736, 1662, 1474, 1368, 1360, 1156; MS m/z (MH+−HCl), calcd for $C_{11}H_{21}N_2O_3 \cdot HCl$: 229.1552, obsd 229.1559.

C:
N-(5-Dimethylamino-1-naphthalenesulfonyl)-glycyl-L-proline tert-butyl ester.

5-Dimethylamino-1-naphthalenesulfonyl chloride (5.10 g, 18.9 mmol) was added in portions to a well-stirred solution of glycyl-L-proline tert-butyl ester hydrochloride (5.00 g, 18.9 mmol) and triethylamine (5.20 mL, 37.8 mmol) in dry tetrahydrofuran (175 mL). The mixture was stirred at room temperature for 4 hours before it was diluted with ethyl acetate and washed successively with saturated sodium bicarbonate solution and brine. Following drying and solvent evaporation, the residue was chromatographed on silica gel (gradient elution with first 40% ethyl acetate in hexanes followed by 50% ethyl acetate in hexanes) and furnished 7.62 g (87%) of the title compound as a fluorescent green foam, m.p. 60°-67° C.; $^1$H NMR (CDCl$_3$) δ 8.51 (dd, J=8.5, 3.3 Hz, 1H), 8.30 (d, J=8.7 Hz, 1H), 8.21-8.16 (m, 1H), 7.58-7.43 (m, 2H), 7.15 (d, J=7.4 Hz, 1H), 5.85-5.79 (m, 1H), 4.27-4.23 (m, 1H), 3.76-3.62 (m, 2H), 3.48-3.21 (m, 2H), 2.84 (s, 6H), 2.10-1.75 (m, 4H), 1.33 and 1.32 (2s, 9H); $^{13}$C NMR (CDCl$_3$) ppm 170.84, 170.45, 165.84, 165.46, 152.04, 134.31, 134.16, 130.79, 130.16, 130.12, 129.87, 129.52, 129.47, 128.77, 123.23, 123.17, 119.22, 119.13, 115.59, 83.00, 81.82, 59.99, 59.38, 46.97, 45.98, 45.64, 44.69, 44.58, 31.41, 29.13, 28.05, 27.96, 24.49, 23.80, 22.36; IR (KBr, cm$^{-1}$) 3266, 2978, 2942, 2876, 2834, 1736, 1658, 1456, 1440, 1370, 1330, 1148, 792, 626, 574; MS m/z (MH+) calcd 461.1984, obsd 461.1982.

Anal. Calcd for $C_{23}H_{30}N_3O_5S$: C, 59.61, H, 6.79, N, 9.07.

Found: C, 59.66; H, 6.87; N, 9.02.

D:
N-(5-Dimethylamino-1-naphthalenesulfonyl)-glycyl-L-proline Hydrochloride

A cold (0° C.), saturated solution of hydrogen chloride in dioxane (400 mL) was added to N-(5-dimethylamino-1-naphthalenesulfonyl)-glycyl-L-proline tert-butyl ester (7.20 g, 15.6 mmol). The mixture was stirred at about 0° C. for about 2 hours and at room temperature for about 2 hours before ether (100 mL) was added. After refrigeration for about 1 hour, the mixture was suction-filtered and afforded 8.30 g (99%) of the title compound as a dense, white solid, m.p. 115°-135° C. (sealed tube); $^1$H NMR (D$_2$O) δ 8.53 (d, J=8.8 Hz, 1H), 8.30 (d, J=8.7 Hz, 1H), 8.10 (d, J=7.4 Hz, H), 7.95 (d, J=7.8 Hz 1H), 7.74-7.67 (m, 2H), 3.84-3.67 (m, 2H), 3.61 (s, 6H), 3.32-3.17 (m, 2H), 1.96-1.87 (m, 1H), 1.77-1.67 (m, 3H); —C NMR (D$_2$O) ppm 178.17, 178.03, 170.68, 170.34, 141.10, 137.84, 137.61, 133.07, 132.88, 131.39, 130.65, 129.57, 129.24, 128.50, 128.41, 128.11, 122.13, 61.88, 49.52, 49.27, 46.82, 33.44, 31.34, 26.84, 24.32; IR (KBr, cm$^{-1}$) 3432, 3070, 2960, 1736, 1654, 1440, 1328, 1178, 1146, 1120, 872, 772, 586; MS m/z (MH+−HCl) calcd 406.1437, obsd 406.1450.

Anal. Calcd for $C_{19}H_{23}N_3O_5S \cdot 1.0HCl \cdot 1.0Dioxane \cdot 0.5H_2O$: C, 51.25; H, 6.18; N, 7.80; H$_2$O, 1.6.

Found: C, 51.01; H, 6.30; N, 7.53; H$_2$O, 1.8.

E: Nα-(5-Dimethylamino-1-naphthalenesulfonyl)-glycyl-L-propyl]-Nδ-benzyloxycarbonyl-L-arginine lactam Isobutyl chloroformate (1.43 mL, 11.04 mmol) was added dropwise to a cold (−20° C.) solution of N-(5-dimethylamino-1-naphthalenesulfonyl)-glycyl-proline hydrochloride (4.88 g, 11.04 mmol) and N-methylmorpholine (2.4 mL, 22.1 mmol) in dry tetrahydrofuran (200 mL). After about 20 minutes at about −20° C., a cold (−20° C.) solution of Nα-benzyloxycarbonyl-L-arginine lactam dihydrochloride (4.00 g, 11.04 mmol) and triethylamine (4.60 mL, 33.12 mmoles) in dry tetrahydrofuran (200 mL) was canulated into the reaction mixture. The mixture was stirred at about −20° C. for about 1 hour before it was allowed to warm up and stir at room temperature for an additional two hours. The mixture was then diluted with ethyl acetate and washed successively with saturated sodium bicarbonate solution and brine prior to drying and solvent evaporation. Purification of the residue by flash chromatography (elution with absolute ethyl acetate) gave 2.17 g (29%) of the title compound as a white solid, m.p. 177°–179° C.; $^1$H NMR (CD$_3$SOCD$_3$) δ 9.54 (br s, 1H), 9.13 (br s, 1H), 8.45–8.39 (m, 1H), 8.36–8.29 (m, 1H), 8.18–8.11 (m, 1H), 8.03–8.00 (m, 1H), 7.62–7.54 (m, 2H), 7.36–7.26 (m, 5H), 7.23 (d, J=7.5 Hz, 1H), 5.04 (s, 2H), 4.51–4.42 (m, 1H), 4.35–4.14 (series of m, 2H), 3.77–3.68 (m, 2H), 3.64–3.57 (m, 1H), 3.44–3.31 (m, 1H), 2.81–2.80 (2s, 6H), 2.11–1.51 (series of m, 8H); $^{13}$C NMR (CD$_3$SOCD$_3$) ppm 175.29, 175.06, 171.44, 171.35, 166.14, 165.83, 162.81, 159.55, 151.29, 137.05, 136.39, 136.26, 129.32, 129.16, 129.06, 128.38, 127.98, 127.82, 123.60, 123.53, 119.42, 115.11, 66.10, 59.49, 58.88, 50.60, 50.45, 46.83, 45.81, 45.09, 44.53, 44.10, 42.88, 42.55, 37.40, 31.75, 29.22, 24.78, 24.05, 22.00, 19.88; IR (KBr, cm$^{-1}$) 3352, 3178, 2942, 1692, 1680, 1656, 1642, 1612, 1504, 1440, 1310, 1262, 1144, 788, 628, 572; MS m/z (MH+) calcd 678.2710, obsd 678.2691.

Anal. Calcd for C$_{33}$H$_{39}$N$_7$O$_7$S: C, 58.48; H, 5.80; N, 14.47.

Found: C, 58.36; H, 5.76; N, 14.35.

F: Nα-[N-(5-Dimethylamino-1-naphthalenesulfonyl)-glycyl-L-prolyl]-Nδ-benzyloxycarbonyl-L-arginine aldehyde Obtained 0.78 g (43%), fluorescent-green foam, m.p. 105°–115° C. $^1$H NMR (CD$_3$SOCD$_3$) δ 8.38 (d J=8.4 Hz, 1H), 8.20–8.16 (m, 1H), 8.09–8.02 (m, 1H), 7.57–7.50 (m, 2H), 7.26–7.23 (m, 5H), 7.17 (d, J=7.6 Hz, 1H), 5.75 (m, 1H), 4.96–4.83 (m, 2H), 3.68–3.54 (m, 2H), 3.33–2.91 (series of m, 2H), 2.66 (s, 6H), 1.79–1.57 (m, 4H), 1.45–1.29 (m, 2H); —C NMR (CD3SOCD3) ppm 171.86, 171.41, 171.05, 166.34, 166.13, 165.89, 163.17, 160.93, 160.36, 160.24, 151.33, 137.43, 135.55, 135.22, 129.63, 128.91, 128.34, 128.18, 128.10, 127.87, 127.75, 127.67, 127.63, 126.90, 126.56, 123.57, 118.87, 115.16, 74.14, 73.55, 65.65, 62.84, 62.34, 60.18, 59.76, 59.49, 59.11, 58.44, 49.01, 47.36, 46.99, 46.04, 44.93, 44.31, 43.78, 31.71, 29.10, 24.09, 23.86, 23.47, 22.00, 21.74, 20.67, 19.04, 13.90; IR (KBr, cm$^{-1}$) 2944, 2874, 1734, 1652, 1612, 1522, 1454, 1284, 1144, 792, 626, 574; MS m/z (MH+), calcd for C$_{33}$H$_{42}$N$_7$O$_7$S: 680.2866, obsd 680.2848.

G: Nα-[N-(5-Dimethylamino-1-naphthalenesulfonyl)-glycyl-L-prolyl]-L-arginine-aldehyde Dihydrochloride Obtained 611.1 mg (93%), pale yellow, crystalline solid, m.p. 115°–130° C. (sealed tube); $^1$H NMR (D$_2$O) δ 8.62 (d, J=8.7 Hz, 1H), 8.37–8.34 (m, 1H), 8.24–8.13 m, 1H), 8.02–7.99 (m, 1H), 7.81–7.75 (m, 2H), 4.11 (m, 3.98 (m, 1H), 3.88–3.61 (m, 2H), 3.48 (s, 6H), 3.43–3.32 (m, 2H), 3.21–2.93 (m, 1H), 2.13–1.41 (series of m, 10H); $^{13}$C NMR (D$_2$O) ppm 179.32, 177.20, 176.95, 176.65, 176.20, 175.30, 170.98, 160.04, 159.30, 157.14, 141.11, 137.89, 132.96, 131.36, 130.76, 129.62, 129.29, 128.84, 128.24, 125.27, 122.22, 119.20, 106.24, 93.11 79.09, 67.95–21.32 (42 lines); IR (KBr, cm$^{-1}$) 3600–2900, 1654, 1442, 1388, 1326, 1144, 794, 586; MS m/z (MH+−2HCl), calcd 546.2499, obsd 546.2516.

EXAMPLE 21

Nα-[N-(8-Quinolinesulfonyl)-glycyl-L-prolyl]-L-arginine aldehyde Hydrochloride

A: N-(8-Quinolinesulfonyl)-glycyl-L-proline tert-Butyl ester

Obtained 6.60 g (83%), m.p. 150–153° C.; $^1$H NMR (CDCl$_3$) 69.06–9.01 (m, 1H), 8.37–8.31 (m, 1H), 8.22–8.19 (m, 1H), 8.03–8.00 (m, 1H), 7.61–7.56 (m, 1H), 7.54–7.46 (m, 1H), 7.14–7.06 (m, 1H), 4.21–4.10 (m, 1H), 3.83–3.86 (m, 2H), 3.48–3.27 (m, 2H), 2.11–1.73 (m, 4H), 1.31 and 1.26 (2s, 9H); —C NMR (CDCl$_3$ppm 170.93, 170.69, 166.00, 165.58, 151.67, 143.54, 136.93, 136.89, 135.59, 135.47, 133.74, 133.70, 131.13, 131.06, 129.00, 125.55, 125.46, 122.65, 122.54, 82.86, 81.56, 59.85, 59.50, 46.81, 46.16, 45.56, 45.48, 31.45, 29.12, 27.99, 24.54, 22.35; IR (KBr, cm$^{-1}$) 3458, 3306, 3206, 2972, 1742, 1662, 1438, 1390, 1370, 1332, 1220, 1166, 1148, 840, 830, 792; MS m/z (MH+) calcd 420.1593, obsd 420.1594

Anal. Calcd for C$_{20}$H$_{25}$N$_3$O$_5$S: C, 57.26; H, 6.01; N, 10.02.

Found: C, 57.49; H, 6.27; 9.68.

B: N-8-(Quinolinesulfonyl)-glycyl-L-proline Hydrochloride

Obtained 6.86 g (100%), m.p. 95°–155° C. (sealed tube); $^1$H NMR (CDCl$_3$) δ 9.09–9.06 (m, 1H), 8.92–8.89 (m, 1H), 8.44–8.41 (m, 1H), 8.31–8.27 (m, 1H), 7.97–7.91 (m, 1H), 7.82–7.75 (m, 1H), 4.00–3.92 (m, 2H), 3.44–3.29 (m, 2H), 2.08–1.99 (m, 1H), 1.85–1.76 (m, 3H); $^{13}$C NMR (D$_2$O) ppm 178.12, 170.45, 150.56, 149.12, 138.29, 138.16, 137.85, 132.76, 132.18, 130.94, 125.68, 61.90, 49.20, 46.85, 31.38, 26.91; IR (KBr, cm$^{-1}$) 3432, 3082, 2960, 2854, 1736, 1656, 1596, 1552, 1452, 1334, 1166, 1150, 1118, 872; MS m/z (MH+−HCl) calcd 364.0967, obsd 364.0982.

Anal. Calcd for C$_{16}$H$_{17}$N$_4$O$_5$S·1.0HCl·1.0Dioxane·0.4 H$_2$O: C, 48.52; H, 5.46; N, 8.49; H$_2$O, 1.5.

Found: C, 48.33; H, 5.54; N, 8.43; H$_2$O, 1.8.

C: Nα-[N-(8-Quinolinesulfonyl)-glycyl-L-prolyl]-Nδ-benzyloxycarbonyl-L-arginine lactam Obtained 3.76 g (54%), white foam, m.p. 107°–122° C.; $^1$H NMR (CD$_3$SOCD$_3$) 6 9.53 (br s, 1H), 9.07–9.04 (m, 3H), 8.53 (dd, J=8.4, 1.6 Hz, 1H), 8.40–8.10 (series of m, 2H), 7.77–7.67 (m, 2H), 7.37–7.21 (m, 5H), 7.09 (br s, 1H), 5.05–5.03 (m, 2H), 4.47–4.14 (series of m, 2H), 3.93–3.82 (m, 2H), 3.65–3.56 (m, 1H), 3.46–3.16 (series of m, 3H), 1.99–1.55 (series of m, 8H); $^{13}$C NMR (CD₃SOCD₃) ppm 175.25, 175.06, 174.83, 171.27, 171.20, 170.88, 170.38, 165.96, 165.61, 162.81, 159.55, 159.52, 151.35, 142.71, 137.16, 137.04, 135.73, 135.51, 133.64, 128.55, 128.38, 127.99, 127.82, 125.74, 122.58, 66.11, 59.98, 59.80, 59.44, 58.94, 50.57, 50.42, 46.80, 45.65, 44.92, 44.61, 42.95, 42.46, 31.67, 29.27, 24.87, 24.65, 23.93, 21.99, 20.79, 19.83, 14.11; (IR (KBr, cm⁻¹) 3370, 2952, 2880, 1684, 1658, 1612, 1494, 1378, 1264, 1166, 1146, 1106; MS m/z (MH+) calcd 636.2240, obsd 636.2256.

Anal. Calcd for $C_{30}H_{33}N_7O_7S \cdot 0.3H_2O$: C, 56.21; H, 5.29; N, 15.30; $H_2O$, 0.84.

Found: C, 56.18; H, 5.37; N, 15.05; $H_2O$, 0.70.

D:
$N^\alpha$-[N-(8-Quinolinesulfonyl)-glycyl-L-prolyl]-$N^\delta$-benzyloxycarbonyl-L-arginine aldehyde Obtained. 1.07 g (30%), white solid, m.p. 115°–140° C.; ¹H NMR (CD₃SOCD₃) δ 9.06–9.03 (m, 1H), 8.52 (dd, J=6.9, 1.3 Hz, 1H), 8.33–8.24 (m, 2H), 8.04–7.56 (series of m, 3H), 7.34–7.23 (m, 5H), 7.20–7.17 (m, 1H), 6.15–5.73 (series of m, 2H), 5.02–4.90 (m, 2H), 4.39–4.32 and 4.21–4.13 (2m, 1H), 3.89–3.65 (m, 2H), 3.52–2.98 (series of m, 5H), 2.04–1.49 (m, 5H), 1.39–1.26 (m, 2H); ¹³C NMR (CD₃SOCD₃) ppm 171.03, 170.62, 170.38, 165.78, 165.54, 165.40, 165.22, 163.22, 163.25, 161.06, 161.00, 160.44, 160.36, 151.41, 151.33, 142.69, 137.82–122.58 (olefinic, 16 lines), 74.29, 73.64, 65.43, 65.36, 59.80, 59.65, 59.26, 58.93, 58.09, 48.99, 47.15, 46.84, 45.65, 44.92, 44.60, 37.18, 31.65, 29.30, 29.12, 24.07, 23.79, 22.21, 20.79, 19.32, 14.11; IR (KBr, cm⁻¹) 3414, 2948, 2876, 1732, 1652, 1612, 1564, 1454, 1378, 1284, 1166, 1144; MS m/z (MH+) calcd 638.2397, obsd 638.2410.

Anal. Calcd for $C_{30}H_{35}N_7O_7S \cdot 0.2EtOAc \cdot 0.3H_2O$: C, 55.99; H, 5.68; N, 14.84; $H_2O$, 0.82.

Found: C, 55.93; H, 5.61; N, 14.80; $H_2O$, 0.90.

E:
$N^\alpha$-[N-(1,2,3,4-Tetrahydro-8-quinolinesulfonyl-glycyl-L-prolyl]-L-arginine aldehyde Dihydrochloride Obtained 0.80 g (100%), golden-brown foam, m.p. 119°–156° C. (sealed tube); ¹H NMR (D₂O) δ 7.81–7.60 (m, 1H), 7.36–7.32 (m, 1H), 7.05–7.03 (m, 1H), 6.48–6.46 (m, 1H), 3.66–3.02 (series of m, 9H), 2.69 (br s, 2H), 2.48–2.41 (m, 1H), 1.97–1.50 (series of m, 10H); ¹³C NMR (D₂O) ppm 173.56, 173.22, 173.06, 171.83, 170.85, 165.95, 165.69, 157.72, 157.20, 156.45, 156.25, 142.44, 135.04, 133.82, 133.46, 128.57, 128.34, 128.11, 127.49, 124.92, 122.58, 118.77, 113.57, 104.74, 67.71–18.61 (42 lines); IR (KBr, cm⁻¹) 3332, 3158, 2956, 2880, 1654, 1448, 1332, 1164, 1138; MS m/z (MH+ −2HCl), calcd for $C_{22}H_{34}N_7O_5S \cdot 2HCl$: 508.2342, obsd 508.2344.

EXAMPLE 22

$N^\alpha$-[2-[2-Amino-4,5-diphenyl-1-imidazolyl]acetyl]-L-arginine aldehyde Dihydrochloride A: Ethyl 2-[2-Amino-4,5-diphenyl-1-imidazolyl]acetate Ethyl bromoacetate (3.50 mL, 31.87 mmol) was added to a solution of 2-amino-4,5-diphenylimidazole (7.50 g, 31.87 mmol) and 1,8-diazobicyclo[5.4.0]undec-7-ene (4.80 mL, 31.87 mmol) in anhydrous tetrahydrofuran (150 mL). The mixture was heated to about 75° C. for about 2 hours and at about 65° C. for about 16 hours before it was cooled to room temperature and treated with brine. After about 15 minutes, ethyl acetate was added and the organic phase was separated, washed with saturated sodium bicarbonate solution and brine prior to drying and solvent concentration to one quarter volume. The precipitate which formed on concentration of the solvent was collected by suction-filtration. There was isolated 3.67 g (36%) of the title compound as an off-white solid. An additional 2.56 g (25%) of the title compound was isolated from the filtrate on concentration, m.p. 173°–175° C.; ¹H NMR (CD₃SOCD₃) δ 7.46–7.36 (m, 3H), 7.32–7.29 (m, 2H), 7.25–7.21 (m, 2H), 7.17–7.04 (m, 2H), 7.03–6.99 (m, 1H), 5.78 (s, 2H), 4.36 (s, 2H), 4.03 (q, J=7.1 Hz, 2H), 1.08 (t, J=7.1 Hz, 3H); ¹³C NMR (CD₃SOCD₃) ppm 170.07, 151.51, 137.08, 133.74, 133.02, 132.50, 130.74, 130.01, 129.59, 128.55, 127.26, 127.06, 124.83, 62.62, 45.71, 15.69; IR (KBr, cm⁻¹) 3410, 3390, 3062, 2980, 1744, 1660, 1562, 1476, 1340, 1240, 1222, 1212, 1026, 772, 700; MS m/z (MH+) calcd 322.1556, obsd 322.1555.

Anal. Calcd for $C_{19}H_{19}N_3O_2$: C, 71.01; H, 5.96; N, 13.07.

Found: C, 70.71; H, 5.89; N, 12.95.

B: 2-[2-Amino-4,5-diphenyl-1-imidazolyl]acetic acid

Obtained 4.33 g (83%), off-white solid, m.p. 218°–224° C. (dec.); ¹H NMR (CD₃OD/CF₃CO₂D) δ 7.53–7.41 (m, 3H), 7.32–7.25 (m, 2H), 7.22 (s, 5H), 4.47 (s, 2H); ¹³C NMR (CD₃OD/CF₃CO₂D) ppm 170.02, 148.99, 132.30, 131.60, 131.22, 130.73, 129.93, 129.76, 128.62, 127.79, 125.53, 124.67, 45.40; IR (KBr, cm⁻¹) 3310, 3052, 1686, 1602, 1380, 1300, 764, 696; MS m/z (MH+) calcd 294.1243, obsd 294.1253.

Anal. Calcd for $C_{17}H_{15}N_3O_2$: C, 64.60; H, 5.59; N, 13.30.

Found: C, 64.89; H, 5.50; N, 13.01.

C:
$N^\alpha$[-2-[2-Amino-4,5-diphenyl-1-imidazolyl]acetyl]-$N^\alpha$-benzyloxycarbonyl-L-arginine lactam Triethylamine (5.70 mL, 40.68 mmol) was added in one portion to a well-stirred mixture of $N^\delta$-benzyloxycarbonyl-L-arginine lactam dihydrochloride (4.91 g, 13.56 mmol), 2-[2-amino-4,5-diphenyl-1-imidazolyl]acetic acid (3.98 g, 13.56 mmol) and benzotriazo-1-yloxytris(dimethylamino)phosphonium hexafluorophosphate (6.00 g, 13.56 mmol) in anhydrous dimethylformamide/acetonitrile (300 mL, 2:1). After about 20 hours at ambient temperature, the solvent was removed in vacuo and the residue was partitioned between ethyl acetate and saturated sodium bicarbonate solution. The organic phase was then separated, washed with brine, dried and concentrated. Purification of the residue by gravity chromatography on silica gel (elution with absolute ethyl acetate) provided 1.71 g (22%) of the title compound as an offwhite solid, m.p. 178°–184° C.; ¹H NMR (CD₃SOCD₃) δ 9.58 (br s, 1H), 9.17 (br s, 1H), 8.27 (d, J=7.8 Hz, 1H), 7.45–7.27 (m, 12H), 7.14–7.09 (m, 2H), 7.04–6.99 (m, 1H), 5.57 (s, 2H), 5.04 (s, 2H), 4.62–4.53 (m, 1H), 4.27–4.19 (m, 3H), 3.69–3.58 (m, 1H), 2.02–1.94 (m, 1H), 1.89–1.67 (m, 2H), 1.65–1.53 (m, 1H); ¹³C NMR (CD₃SOCD₃) ppm 175.10, 167.29, 162.80, 159.58, 149.95, 137.05, 13 5.57, 131.91, 131.31, 130.84, 128.97, 128.38, 12 8.04, 127.96, 127.85, 127.82, 125.66, 125.28, 12 3.60, 66.10, 50.76, 45.26, 42.75, 24.92, 19.75; IR (KBr, cm⁻¹) 3386, 3060, 2940, 1680, 1612, 1500, 1298, 1264, 1192, 700; MS m/z (MH+) calcd 566.2516, obsd 566.2532.

Anal. Calcd for $C_{31}H_{31}N_7O_4$: C, 65.33; H, 5.69; N, 16.57.

Found: C, 65.04; H, 5.66; N, 16.29.

D:
N$^\alpha$-[2-[2-Amino-4,5-diphenyl-1-imidazolyl]acetyl]-N$^\delta$-benzyloxycarbonyl-L-arginine aldehyde Obtained 394 mg (66%), off-white solid, m.p. 173°–181° C. (dec.); $^1$H NMR (CD$_3$SOCD$_3$) δ 8.20 (br s, 1H), 7.85 and 7.61 (2d, J=8.2, 8.5 Hz, 1H), 7.44–7.18 (m, 12H), 7.13–7.08 (m, 2H), 7.03–6.99 (m, 1H), 6.02 and 5.97 (2br s, 2H), 5.55 and 5.48 (2s, 2H), 5.01–4.92 (m 2H), 4.17 ( s, 2H), 3.66–3.64 (m, 1H), 3.04–2.96 (m, 1H), 1.67–1.32 (series of m, 4H); $^{13}$C NMR (CD$_3$SOCD$_3$) ppm 167.15, 166.65, 163.34, 163. 23, 161.73, 160.28, 150.06, 149.89, 137.78, 135.60, 131.79, 131.42, 130.80, 130.64, 128.92, 128.35, 128.29, 128.04, 127.90, 127.84, 127.55, 125.70, 125.62, 125.23, 123.51, 74.58, 73.79, 65.45, 62. 83, 59.79, 49.02, 47.43, 45.21, 37.56, 37.06, 24.15, 23.79, 22.38, 20.79, 19.05, 14.12; IR (KBr, cm$^{-1}$) 3406, 2942, 1660, 1602, 1520, 1284, 1030, 698; MS m/z (MH+) calcd 568.2672, obsd 568.2685.

Anal. Calcd for C$_{31}$H$_{33}$N$_7$O$_4$·0.25EtOAc·0.10H$_2$O: C, 64.99; H, 6.00; N, 16.58; H$_2$O, 0.31.

Found: C, 64.75; H, 6.03; N, 16.30; H$_2$O, 0.00.

E:
N$^\alpha$-[2-[2-Amino-4,5-diphenyl-1-imidazolyl]acetyl]-L-arginine aldehyde Dihydrochloride Obtained 485 mg (85%), off-white solid, m.p. 153°–210° C.; $^1$H NMR (D$_2$O) δ 7.40–7.37 (m, 1H), 7.31–7.26 (m, 2H), 7.11–7.03 (m, 7H), 4.52–4.34 (m, 1H), 3.90–3.86 (m, 1H), 3.15 (br s, 1H), 1.53–1.49 (m, 1H), 1.21 (br s, 2H); $^{13}$C NMR (D$_2$O) ppm 170.26, 170.00, 169.65, 159.30, 149.78, 133.58, 133.09, 132.99, 132.15, 131.54, 131.35, 129.63, 129.13, 128.65, 126.76, 125.61, 79.95, 79.19, 56.95, 52.32, 50.82, 48.11, 47.89, 43.45, 43.22, 42.56, 28.37, 27.29, 25.45, 25.37, 24.25, 21.18, 14.95, 11.90; IR (KBr, cm$^{-1}$) 3500–2900, 1668, 1534, 1446, 766, 696; MS m/z (MH+−2HCL) calcd 434.2304, obsd 434. 2318.

Anal. Calcd for C$_{23}$H$_{27}$N$_7$O$_2$·2.0HCl·2.1H$_2$O: C, 50.76; H, 6.15; N, 18.02; H$_2$O 6.95.

Found: C, 50.49; H, 5.90; N, 17.50; H$_2$O, 4.84.

EXAMPLE 23

N$^\alpha$-[L-Tyrosyl-L-prolyl]-L-arginine aldehyde Dihydrochloride

A:
N$^\alpha$-[O-Benzyl-N-benzyloxycarbonyl-L-tyrosyl-L-prolyl]-N$^\delta$-benzyloxycarbonyl-L-arginine lactam Obtained 2.19 g (43%), white foam, m.p. 68°–74° C.; $^1$H NMR (CD$_3$SOCD$_3$) δ 9.12 (br s, 1H), 8.11 and 7.56 (2d, J=7.8, 8.3 Hz, 2H), 7.40–7.05 (m, 19H), 6.89–6.81 (m, 2H), 5.00 (4H), 4.89 (s, 2H), 4.60–4.51 (m, 1H), 4.38–4.30 (m, 2H), 3.62–3.32 ( 2m, 3H), 2.90–2.59 (series of m, 3H), 2.03–1.60 (series of m, 8H); $^{13}$C NMR (CD$_3$SOCD$_3$) ppm 175.55, 171.65, 171.40, 170.31, 162.88, 159.53, 157.08, 156.01, 137.31, 137.11, 130.44, 130.20, 128.50, 128.43, 128.05, 127.87, 127.72, 127.63, 127.46, 114.53, 72.53, 69.23, 66.17, 65.35, 59.46, 54.66, 50.44, 46.82, 42.80, 42.22, 35.67, 29.17, 24.57, 19.84; IR (KBr, cm$^{-1}$) 3368, 3032, 2950, 1704, 1640, 1612, 1512, 1454, 1298, 1264, 1178, 1158, 1108, 740, 698; MS m/z (MH+) calcd 775.3455, obsd 775.3447.

Anal. Calcd for C$_{43}$H$_{46}$N$_6$O$_8$·0.95H$_2$O: C, 65.21; H, 6.10; N, 10.61; H$_2$O, 2.16.

Found: C, 65,20; H, 6.04; N, 9.98; H$_2$O, 0.86.

B:
N$^\alpha$-[O-Benzyl-N$^\delta$-benzyloxycarbonyl-L-tyrosyl-L-prolyl]-N$^\delta$-benzyloxycarbonyl-L-arginine aldehyde Obtained 0.878 g (56%), pale yellow solid, m.p. 82°–92° C.; $^1$H NMR (CD$_3$SOCD$_3$) δ 8.10–7.55 (series of m, H), 7.44–7.14 (m, 19H), 6.89 (d, J=8.6 Hz, 2H), 6.16–5.80 (m, 2H), 5.04 (s, 2H), 5.00–4.92 (m, 4H) 4.49–4.29 (m, 2H), 3.83–3.54 (2m, 3H), 3.36 (s, 1H), 3.13–2.67 (series of m, 3H), 1.97–1.43 (series of m, 8H); $^{13}$C NMR (CD$_3$SOCD$_3$) ppm 171.27, 170.58, 170.38, 170.01, 163.30, 161.18, 160.46, 157.03, 155.98, 137.96–126.45, (15 lines, olefinic), 114.47, 74.48, 73.77, 69.19, 68.56, 65.46, 65.39, 65.30, 59.27, 59.01, 55.86, 54.68, 48.96, 47.25, 46.76, 37.21, 35.63, 29.64, 29.06, 28.85, 24.62, 24.35, 24.21, 23.84, 22.26, 19.39: IR (KBr, cm$^{-1}$) 2948, 2874, 1716, 1642, 1612, 1512, 1454, 1282, 1240, 738, 698; MS m/z (MH+) calcd 777.3612, obsd 777.3613. Anal. Calcd for C$_{43}$H$_{48}$N$_6$O$_8$·0.6H$_2$O: C, 65.57, H, 6.30; N, 10.67; H$_2$O, 1.37. Found: C, 65.26; H, 6.10; N, 10.50; H$_2$O, 1.15.

C: N$^\alpha$-[L-Tyrosyl-L-prolyl]-L-arginine aldehyde Dihydrochloride

Obtained 435.8 mg (97%), pale-yellow solid, m.p. 145°–165° C. (decomp. pt. 175° C., sealed tube); $^1$H NMR (D$_2$O) δ 7.36–7.12 (m, 4H), 5.40–5.32 (m, 0.5H), 4.96–4.86 (m, 0.25H), 4.40–4.27 (m, 1H), 4.01–3.73 (m, 1H), 3.49–3.40 (m, 3H), 3.29–3.07 (m, 1H), 2.64–2.57 (m, 2H), 2.34–1.48 (series of m, 8H); −C NMR (D$_2$O) ppm 176.89, 176.80, 176.05, 159.30, 143.98, 130.61, 130.49, 128.13, 92.49, 78.48, 62.40, 62.22, 62.03, 55.78, 51.38, 49.99, 49.27, 42.81, 42.18, 41.92, 36.34, 35.14, 33.91, 31.80, 27.96, 27.87, 27.66, 26.36, 24.82, 24.68, 24.39; IR (KBr, cm$^{-1}$) 3600–2850, 1652, 1614, 1596, 1516, 1450, 1364, 1238; MS m/z (MH+−2HCL), calcd for C$_{20}$H$_{31}$N$_6$O$_4$·2HCL: 419. 2407, obsd 419.2398.

EXAMPLE 24

N$^\alpha$-[D-Phenylalanyl-L-arginine aldehyde Sulfate

A:
N$^\alpha$-[Benzyloxycarbonyl-D-phenylalanyl]-benzyloxycarbonyl-L-arginine lactam Obtained 5.59 g (64%), white solid, m.p. 113°–118° C.; $^1$H NMR (CD$_3$SOCD$_3$) δ 9.60 (br s, 1H), 9.16 (br s, 1H), 8.43 (d, J=7.6 Hz, 1H), 7.55 (d, J=8.8 Hz, 1H), 7.37–7.21 (m, 15H), 5.04 (s, 2H), 4.98–4.88 (m, 2H), 4.58–4.50 (m, 1H), 4.31–4.24 (m, 2H), 3.66–3.61 (m, 1H), 3.33 (s, 3H), 3.01–2.95 (m, 1H), 2.79–2.71 (m, 1H), 1.98–1.90 (m, 1H), 1.81–1.75 (m, 2H), 1.65–1.54 (m, 1H); $^{13}$C NMR (CD$_3$SOCD$_3$) ppm 175.23, 171.43, 162.91, 159.67, 155.89, 138.07, 137.15, 137.13, 129.34, 129.19, 128.44, 128.37, 128.13, 128.04, 127.88, 127.74, 127.60, 127.46, 126.35, 66.17, 65.26, 56.13, 50.82, 42.73, 37.82, 25.10, 19.77; IR (KBr, ) 3314, cm$^{-1}$) 3062, 3032, 2952, 1696, 1656, 1608, 1530, 1498, 1454, 1258, 1194, 1180, 1164, 1106, 1042, 748, 698; MS m/z (MH+) calcd 572.2509 obsd 572.2497.

Anal. Calcd for C$_{31}$H$_{33}$N$_5$O$_6$: C, 65.14; H, 5.82; N, 12.25.

Found: C, 64.97; H, 5.60; N, 11.95.

B:
N$^\alpha$-[Benzyloxycarbonyl-D-phenylalanyl]-N$^\delta$-benzyloxycarbonyl-L-arginine aldehyde Obtained. 1.01 g (33%), white foam, m.p. 68°–80° C.; $^1$H NMR (CD$_3$SOCD$_3$) δ 7.94–7.79 (m, 2H), 7.52–7.47

(m, 1H), 7.33–7.16 (m, 15H), 6.12–5.66 (series of m, 2H), 5.09–4.91 (m, 4H), 4.39–4.28 (m, 1H), 3.89 and 3.64 (2m, 2H), 3.35 (s, 1H), 3.24–2.82 (m, 2H), 2.75–2.67 (m, 1H), 1.66–1.58 (m, 2H), 1.42–1.28 (m, 2H); —C NMR (CD$_3$SOCD$_3$) ppm. 170.89, 160.39, 155.79, 138.14, 137.86, 137.15, 129.40, 128.35, 128.02, 127.95, 127.71, 127.58, 127.47, 126.26, 74.01, 65.48, 65.20, 56.09, 48.97, 47.20, 37.96, 37.16, 24.18, 23.85; IR (KBr cm$^{-1}$) 3312, 3064, 3032, 2946, 1708, 1658, 1604, 1522, 1454, 1284, 1086, 744, 698; MS m/z (MH+) calcd 574.2666, obsd 574.2668.

Anal. Calcd for $C_{31}H_{35}N_5O_6 \cdot 0.76H_2O$: C, 63.40; H, 6.27; N, 11.93; H$_2$O, 2.33.

Found: C, 63.25; H, 5.97; N, 11.70; H$_2$O, 2.33.

C: N$^\alpha$-[D-Phenylalanyl]-L-arginine aldehyde Sulfate

Obtained 506.7 mg (85%), pale-yellow solid, m.p. 167°–177° C. (dec., sealed tube); $^1$H NMR (D$_2$O) δ 7.39–7.12 (m, 5H), 4.36–4.13 (m, 1H), 3.77 (m, 0.5H), 3.50–2.85 (series of m, 5H), 1.82–0.83 (series of m, 3H); —C NMR (D$_2$O) ppm 180.87, 170.50, 169.48, 159.17, 158.59, 136.05, 135.77, 131.57, 131.37, 131.33, 131.00, 130.14, 129.88, 129.73, 92.06, 78.00, 57.78, 56.64, 56.32, 56.04, 51.53, 49.96, 49.67, 43.28, 42.62, 42.41, 41.80, 38.85, 38.60, 36.66, 31.10, 27.22, 25.84, 24.83, 24.55, 24.16; IR (KBr, cm$^{-1}$) 3358–2700, 1496, 1114, 750, 700, 618; MS m/z (MH+−H$_2$SO$_4$), calcd for $C_{15}H_{24}N_5O_2$-H$_2$SO$_4$ 306.1930, obsd 306.1926.

EXAMPLE 25

N$^\alpha$-[N-(3-Phenylpropanoyl)-glycyl]-L-arginine aldehyde Hydrochloride Hydrate B:
N$^\alpha$-[N-(3-Phenylpropanoyl)-glycyl-N$^\delta$-benzyloxycarbonyl-L-arginine aldehyde White foam, m.p. 69°–74° C.; $^1$H NMR (DMSO-d$_6$) δ 8.08–8.04 (m, 2H), 7.77–7.60 (dd, 1H), 7.33–7.12 (m, 10H), 5.89 (bs, 1H), 4.99–4.90 (m, 2H), 3.70–3.64 (m, 4H), 3.34 (bs, 1H), 3.03–2.95 (m, 1H), 2.81–2.74 (m, 2H), 2.48–2.37 (m, 2H), 1.68–1.64 (m, 2H), 1.50–1.37 (m, 3H); $^{13}$C NMR (DMSO-d6) ppm 177.38, 176.87, 173.79, 173.37, 168.43, 166.81, 166.58, 146.54, 143.05, 133.45, 133.38, 133.23, 133.09, 133.00, 132.72, 131.05, 80.08, 78.91, 70.64, 70.58, 64.96, 54.09, 52.35, 47.13, 42.70, 42.29, 41.96, 36.20, 34.79, 29.23, 28.98, 26.42, 25.95, 24.34, 19.27; IR (KBr, cm $^{-1}$) 3320, 2950, 1725, 1660, 1610, MS m/z (MH+) 482.

Anal. Calcd for $C_{25}H_{31}N_5O_5$: C, 60.11; H, 6.61; N, 14.02.

Found: C, 60.88; H, 6.43; N, 13.48.

C: N$^\alpha$-[N-(3-Phenylpropanoyl)-glycyl]-L-arginine aldehyde Hydrochloride Hydrate Off-white foam, m.p. 95°–118° C. (dec.); $^1$H NMR (D$_2$O) δ 7.5–7.10 (m, 5H), 5.34–5.21 and 4.6 (m, 1H), 3.81–3.65 (m, 3H), 3.38–3.13 (m, 1H), 3.05–3.01 (m, H), 2.86–2.75 (m, 2H), 2.57–2.45 (m, 2H), 1.77–1.52 (m, 3H); $^1$C NMR (D$_2$O) ppm 204.39, 178.54, 178.29, 173.75, 173.56, 173.02, 172.66, 159.96, 159.27, 158.54, 130.84–128.29 (8 lines), 92.28, 79.63, 78.35, 55.85, 51.04, 49.73, 44.59, 44.41, 42.66, 41.85, 38.88, 38.78, 32.57, 32.91, 27.72, 26.29, 24.53, 24.12; IR (KBr, cm$^{-1}$) 3350, 1660, 1590, 1225; MS m/z (MH+) 348.

EXAMPLE 26

N$^\alpha$-[N-(3-Phenylpropanoyl)-glycyl]-L-arginine alcohol Hydrochloride Hydrate Off-white foam; $^1$H NMR (D$_2$O) δ 7.32–7.23 (m, 5H), 3.82 (m, 1H), 3.75 (bs, 2H), 3.6–3.4 (m, 2H), 3.06 (bs, 2H), 2.90–2.85 (t, 2H), 2.61–2.56 (t, 2H), 1.65–1.30 (m, 4H); $^{13}$C NMR (D$_2$O) ppm 178.28, 173.37, 158.56, 142.51, 130.71, 130.31, 128.47, 94.81, 67.97, 65.38, 52.95, 44.69, 42.76, 42.52, 38.35, 32.96, 29.21, 26.42, 16.15; MS m/z (MH+) 350.

Anal. Calcd for $C_{17}H_{27}N_5O_3$: C, 50.55; H, 7.49; N, 17.34.

Found: C, 50.34; H, 7.19; N, 16.19.

EXAMPLE 27

N$^\alpha$-[3-(4,5-Diphenyl-2-oxazolyl)propanol]-L-arginine aldehyde Hydrochloride Hydrate A:
N$^\alpha$-[3-(4,5-Diphenyl-2-oxazolyl)propanoyl]-N$^\delta$-benzyloxycarbonyl-L-arginine lactam.

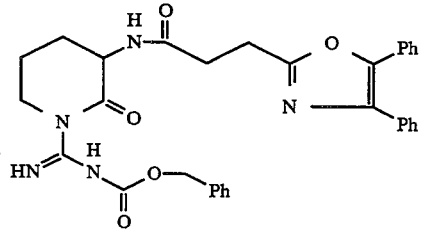

$^1$H NMR (CDCl$_3$) δ 9.55 (bs, 1H), 9.35 (bs, 1H), 7.62–7.52 (m, 4H), 7.39 (m, 11H), 6.92–6.89 (d, 1H), 5.12 (s, 2H), 4.90–4.83 (m, 1H), 4.69–4.60 (m, 1H), 3.41–3.31 (m, 1H), 3.22–3.17 (m, 2H), 2.91–2.77 (m, 2H), 2.54–2.42 (m, 1H), 2.02–1.76 (m, 2H), 1.50–1.36 (m, 1H); —C NMR (CDCl$_3$) ppm 175.69, 171.31, 163.66, 162.12, 159.96, 145.52, 136.22–126.47 (12 lines), 67.2, 51.15, 41.24, 32.92, 24.86, 23.89, 19.53; IR (KBr, cm$^{-1}$) 3380, 3320, 1680, 1650, 1630, 1520, 1260; MS m/z (MH+) 566.

Anal. Calcd for $C_{32}H_{31}N_5O_5$: C, 67.95; H, 5.52; N, 12.38.

Found: C, 67.70; H, 5.49; N, 12.25.

B:
N$^\alpha$-[3-(4,5-Diphenyl-2-oxazolyl)propanoyl]-N$^\delta$-benzyloxycarbonyl-L-arginine aldehyde

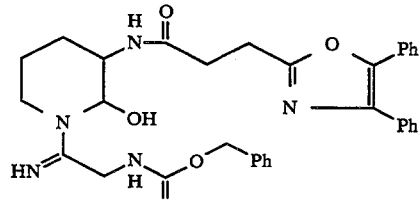

White foam; $^1$H NMR (CDCl$_3$) δ 7.58–6.95 (m, 15H), 5.07–4.98 (m, 2H), 3.89 (bm, 1H), 3.13–2.99 (m, 3H), 2.68–2.60 (m, 2H), 1.80–1.49 (m, 4H); —C NMR (CDCl$_3$) ppm 170.80, 163.80, 162.34, 161.74, 145.48, 137.11–126.42 (12 lines), 95.04, 66.73, 60.41, 49.03, 38.72, 32.88, 24.18, 23.93, 23.42, 21.05, 14.18; IR (KBr, cm$^{-1}$) 3380, 1660, 1600, 1530, 1280; MS m/z (MH+) 568.

Anal. Calcd for $C_{32}H_{33}N_5O_5 \cdot H_2O$: C, 65.63; H, 6.02; N, 11.96.

Found: C, 65.41; H, 5.85; N, 11.36.

C:

$N^{\alpha}$-[3-(4,5-Diphenyl-2-oxazolyl)propanoyl]-L-arginine aldehyde Hydrochloride Hydrate

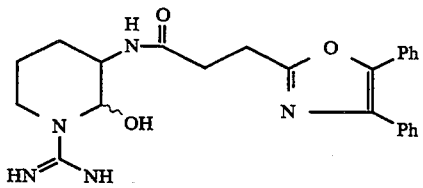

White foam, m.p. 100°–110° C. (dec.); $^1$H NMR (D$_2$O) δ 7.11–6.65 (m, 15H), 5.38 (bs, 1H), 4.00–3.71 and 3.47–3.57 (m, 1H), 3.22–3.14 (m, 1H), 2.89 (bs, 3H), 2.66–2.60 (bm, 2H), 1.63–1.78 (m, 4H); $^{13}$C NMR (D$_2$O) ppm 175.10, 174.61, 164.90, 159.25, 146.77, 136.06, 133.27, 130.34, 130.16, 130.05, 129.50, 127.80, 92.42, 78.52, 67.92, 51.43, 42.79, 41.82, 33.84, 26.38, 25.30, 24.86, 22.38, 16.12; IR (KBr, cm$^{-1}$) 3320, 1650, 1590, 1440; MS m/z (MH+) 434.

Anal. Calcd for $C_{24}H_{27}N_5O_3 \cdot HCl \cdot H_2O$. C, 57.79; H, 6.31; N, 14.04.

Found: C, 58.28; H, 5.92; N, 13.47.

EXAMPLE 28

$N^{\alpha}$-[5-(4,5-Diphenyl-2-oxazolyl)pentanoyl]-L-arginine aldehyde Hydrochloride Hydrate

A:

$N^{\alpha}$-[5-(4,5,Diphenyl-2-oxazolyl)pentanoyl]-$N^{\alpha}$-benzyloxycarbonyl-L-arginine lactam

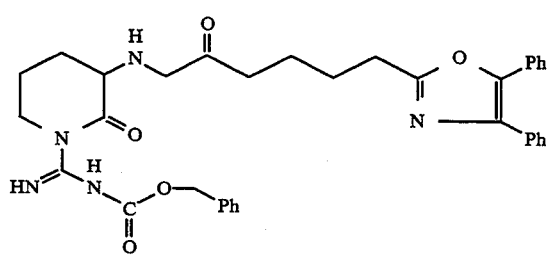

$^1$H NMR (CDCl$_3$) δ 9.60 (bs, 1H), 9.37 (bs, 1H), 7.61–7.24 (m, 15H), 6.58–6.55 (d, 1H), 5.13 (s, 2H), 4.84–4.77 (m, 1H), 4.66–4.57 (m, 1H), 3.43–3.33 (m, 1H), 2.95–2.85 (m, 2H), 2.46–2.30 (m, 3H), 2.03–1.70 (m, 6H), 1.44–1.20 (m, 1H); $^{13}$C NMR (CDCl$_3$) ppm 175.85, 172.53, 163.66, 163.18, 160.00, 145.21, 136.64–126.35 (12 lines), 67.18, 50.90, 41.35, 25.82, 27.76, 26.23, 24.90, 24.88, 19.61; IR (KBr, cm$^{-1}$) 3370, 3310 2920, 1690, 1645, 1620, 1500, 1260; MS m/z (MH+) 594.

Anal. Calcd for $C_{34}H_{35}N_5O_5$: C, 68.78; H, 5.94; N, 11.79.

Found: C, 68.98; H, 5.97; N, 11.67.

B:

$N^{\alpha}$-[5-(4,5-Diphenyl-2-oxazolyl)pentanoyl]-$N^{\delta}$-benzyloxycarbonyl-L-arginine aldehyde

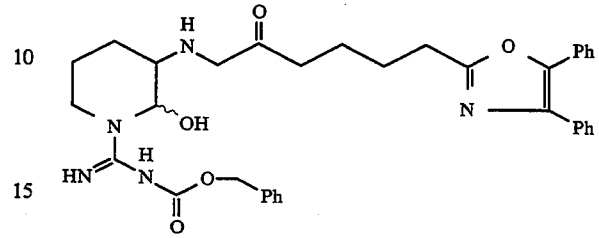

Foam; $^1$H NMR (CDCl$_3$) δ 7.59–7.21 (m, 15H), 6.24–6.07 (m, 1H), 5.69–5.49 (bs, 1H), 5.04 (s, 2H), 3.87 (bs, 1H, 3.53–3.49 (m, 1H), 3.07–2.99 (m, 1H), 2.87–2.78 (m, 2H), 2.17–2.12 (t, 2H), 1.81–1.49 (m, 9H); $^{13}$C NMR (CDCl$_3$) ppm 172.44, 163.96, 163.49, 161.92, 145.41, 137.32–126.55 (13 lines), 75.03, 66.90, 66.03, 49.04, 38.85, 36.17, 27.99, 26.71, 25.23, 24.41, 23.71, 15.45; IR (KBr, cm$^{-1}$) 3350, 2940, 1650, 1610, 1540, 1450, 1280; MS m/z (MH+) 596.

Anal. Calcd for $C_{34}H_{37}N_5O_5$: C, 66.54; H, 6.41; N, 11.41.

Found: C, 66.58; H, 6.19; N, 11.05.

C:

$N^{\alpha}$-[5-(4,5-Diphenyl-2-oxazolyl)pentanoyl]-L-arginine aldehyde Hydrochloride Hydrate

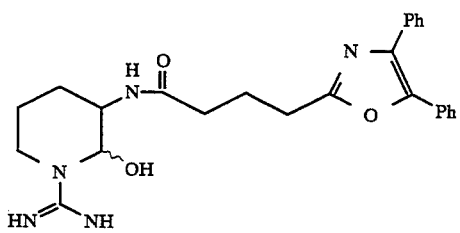

White foam, m.p. 89°–95° C. (dec.); $^1$H NMR (D$_2$O) δ 7.32 (bs, 2H), 6.98–6.92 (d, 5H), 6.64 (bs, 3H), 5.38 (bs, 1H), 3.98–3.70 (m, 1H), 3.54–3.40 (m, 2H), 3.32–3.07 (m, 2H), 2.51 (bs, 2H), 2.18–2.06 (m, 2H), 1.67–1.49 (m, 6H); $^{13}$C NMR (D$_2$O) ppm 176.79, 166.07, 159.28, 146.52, 136.12, 133.39, 130.37, 130.13, 129.49, 127.86, 78.54, 67.94, 51.33, 41.80, 36.92, 29.07, 27.84, 26.77, 24.86; IR (KBr, cm$^{-1}$) 3320, 1650; MS m/z (MH+) 462.

Anal. Calcd for $C_{26}H_{31}N_5O_3 \cdot HCl \cdot H_2O$: C, 60.5; H, 6.6; N, 13.50.

Found: C, 60.94; H, 6.36; N, 13.02.

EXAMPLE 29

Nα-[N-(5-Dimethylamino-1-naphthalenesulfonyl)-L-prolyl]-L-arginine aldehyde Hydrochloride Hydrate A:
Nα-[N-((5-Dimethylamino-1-naphthalenesulfonyl)-L-prolyl]-Nδ-benzyloxycarbonyl-L-arginine lactam

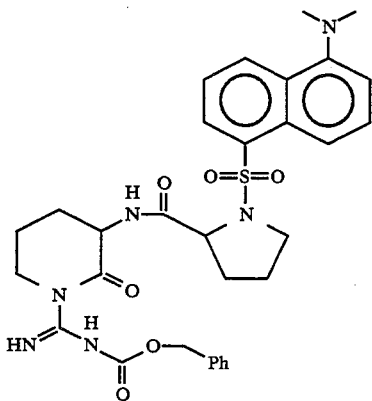

Yellow foam; ¹H NMR (CDCl₃) δ 9.60 (bs, 1H), 9.34 (bs, 1H), 8.54–8.23 (m, 3H), 7.55–7.47 (m, 2H), 7.39–7.11 (m, 8H), 5.11 (s, 2H), 4.72–4.43 (m, 1H), 4.37–4.29 (m, 2H), 3.63–3.26 (m, 3H), 2.82 (s, 6H), 2.32–1.73 (m, 6H), 1.41–1.30 (m, 1H); ¹³C NMR (CDCl₃) ppm 174.55, 171.44, 171.03, 163.51, 159.95, 151.88, 136.57–115.10 (24 lines), 67.01, 62.17, 61.95, 51.18, 50.24, 47.14, 49.07, 45.25, 41.59, 41.29, 31.00, 30.33, 24.62, 24.44, 24.32, 23.85, 19.67, 19.42; MS m/z (MH+) 621.

Anal. Calcd for C₃₁H₃₆N₆O₆S.1.0 H₂O: C, 58.29; H, 6.00; N, 13.16.

Found: C, 58.57; H, 5.66; N, 13.41.

Nα-[N-(5-Dimethylamino-1-naphthalenesulfonyl)-L-prolyl]-Nδ-benzyloxycarbonyl-L-arginine aldehyde

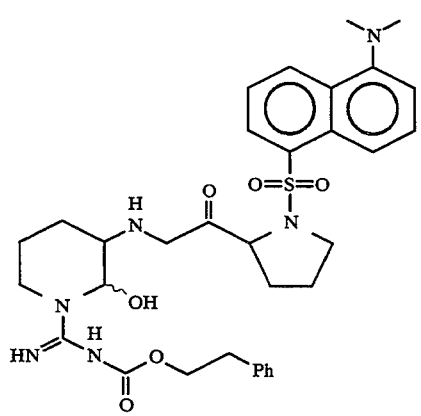

Yellow foam; ¹H NMR (CDCl₃) δ 8.54–8.41 (m, 3H), 7.59–7.02 (m, 8H), 5.66 (bs, 1H), 5.12–5.04 (m, 2H), 4.33–4.23 (m, 1H), 3.84–3.67 (bm, 1H), 3.47–3.29 (m, 2H), 3.07–2.95 (m, 1H), 2.81 (s, 6H), 2.12–2.03 (m, 1H), 1.76–1.41 (m, 6H), 1.24–1.14 (m, 1H); ¹³C NMR (CDCl₃) ppm 171.03, 163.94, 163.84, 161.86, 151.82, 137.34–115.51 (16 lines), 74.75, 66.76, 65.82, 62.21, 61.52, 60.41, 49.45, 49.26, 45.36, 38.73, 33.94, 30.59, 29.23, 24.59, 24.18, 23.45, 15.26, 14.18; IR (KBr, cm⁻¹) 3400, 1660, 1610, 1540; MS m/z (MH+) 623.

Nα-[N-(5-Dimethylamino-1-naphthalenesulfonyl)-L-prolyl]-L-arginine aldehyde Hydrochloride Hydrate

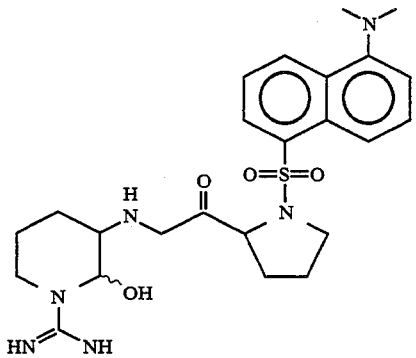

Yellow foam; ¹H NMR (D₂O) δ 8.8–8.71 (m, 1H), 8.47–8.44 (d, 1H), 8.28–8.26 (d, 1H), 8.09–8.07 (d, 1H), 7.89–7.80 (m, 2H), 4.93 (m, 1H), 4.36–4.26 (m, 1H), 3.78–3.14 (m, 10H), 2.15–1.36 (m, 8H); IR (KBr, cm⁻¹) 3400, 1663, 1330, 1140; MS m/z (MH+) 489.

Anal. Calcd for C₂₂H₃₂N₆O₄S.2 HCl.H₂O: C, 48.42; H, 6.18; N, 14.7.

Found: C, 48.41; H, 6.18; N, 14.7.

EXAMPLE 30

(±)Nα-((3-Amino-3-phenyl)propanoyl)-L-prolyl]-L-arginine aldehyde-Hydrochloride Hydrate A:
(±)Nα-[N-(((3-(N-Benzyloxycarbonyl)amino)-3-phenyl)propanoyl)-L-prolyl]-Nδ-benzyloxycarbonyl-L-arginine lactam

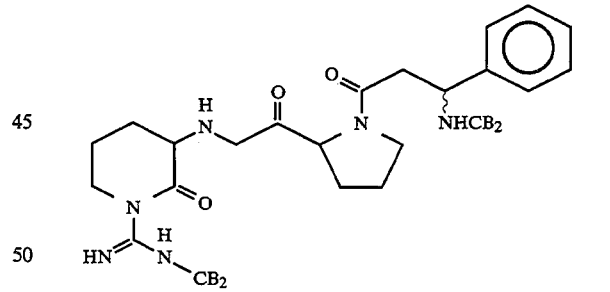

Colorless foam; ¹H NMR (CDCl₃) δ 9.6 (bs, 1H), 9.30 (bs, 1H), 7.47–7.18 (m, 15H), 6.49–6.36 (bs, 1H), 5.14–4.99 (m, 6H), 4.72–4.66 (m, 1H), 4.52–4.37 (m, 2H), 3.5–3.27 (m, 3H), 2.9–2.7 (m, 2H), 2.28–2.18 (m, 3H), 1.91–1.76 (m, 5H); ¹³C NMR (CDCl₃) ppm 175.40, 175.30, 171.06, 170.86, 163.64, 162.55, 160.00, 155.84, 155.68, 141.40, 136.70, 126.44, 128.60–126.15 (13 lines), 67.15, 66.70, 61.24, 59.72, 52.07, 51.16, 50.72, 47.69, 41.59, 40.00, 36.46, 31.93, 31.81, 50.72, 47.69, 41.59, 40.00, 36.46, 31.93, 31.81, 27.45, 27.14, 24.81, 24.74, 24.65, 22.66, 19.72, 19.27; (MH+) 669.

Anal. Calcd for C₃₆H₄₀N₆O₇.H₂O: C, 62.96; H, 6.16; N, 12.24.

Found: C, 62.96; H, 6.16; 12.24.

B: (±) N$^\alpha$-[N-(((3-(N-Benzyloxycarbonyl)amino)-3-phenyl)propanoyl)-L-prolyl]-N$^\delta$-benzyloxy-carbonyl-L-arginine aldehyde

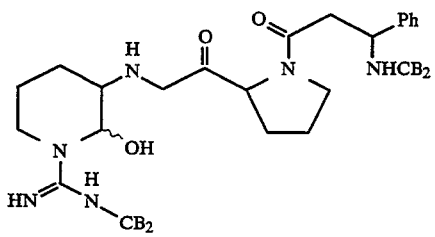

White foam; $^1$H NMR (CDCl$_3$) δ 7.33–7.2 (m, 17H), 6.59–6.51 (m, 1H), 5.74–5.63 (m, 1H), 5.07–4.88 (m, 6H), 4.33–4.27 (m, 1H), 3.74–3.62 (m, 2H), 3.28 (m, 1H), 3.01–2.72 (m, 3H), 2.20–1.53 (m, 9H); IR (KBr, cm$^{-1}$) 3350, 1710, 1610, 1520, 1450, 1270; MS m/z (MH+) 671.

Anal. Calcd for C$_{36}$H$_{42}$N$_6$O$_7$·1.0 H$_2$O: C, 62.78; H, 6.44; N, 12.02.

Found: C, 62.74; H, 6.25; N, 11.76.

C: (±)N$^\alpha$-[N-((3-Amino-3-phenyl)propanoyl)-L-prolyl]-L-arginine aldehyde Hydrochloride Hydrate

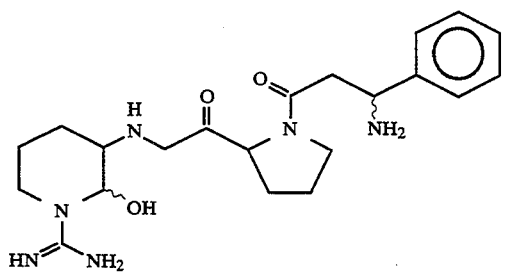

Off-white foam; $^1$H NMR (D$_2$O) δ 7.45 (bs, 5H), 5.40–5.32 (m, 1H), 4.87–4.73 (m, 1H), 4.45–4.26 (m, 1H), 3.99–3.72 (m, 1H), 3.56–3.46 (m, 3H), 3.27–3.17 (m, 3H), 2.24–2.04 (m, 1H), 1.90–1.49 (m, 6H); $^{13}$C NMR (D$_2$O) ppm 176.50, 176.24, 175.82, 171.99, 171.79, 171.61, 159.35, 158.63, 137.30, 131.64, 131.57, 131.39, 129.07, 128.20, 128.64, 92.46, 62.80, 62.50, 62.21, 56.02, 55.95, 53.89, 53.80, 51.49, 50.02, 49.46, 49.36, 45.53, 42.81, 42.77, 42.15, 41.95, 39.67, 39.55, 39.35, 33.92, 31.90, 29.14, 27.56, 26.25, 25.97, 24.81, 24.55, 22.45, 20.67, 20.00; IR (KBr, cm$^{-1}$) 3350, 1660, 1550; MS m/z (MH+) 403.

Anal. Calcd for C$_{20}$H$_{30}$N$_6$O$_3$·2HCl·H$_2$O: C, 48.68; H, 6.95; N, 17.03.

Found: C, 48.87; H, 7.06; N, 16.20.

EXAMPLE 31

N$^\alpha$-[N-(3-Cyclohexylpropyl)-L-prolyl]-L-arginine aldehyde Hydrochloride Hydrate

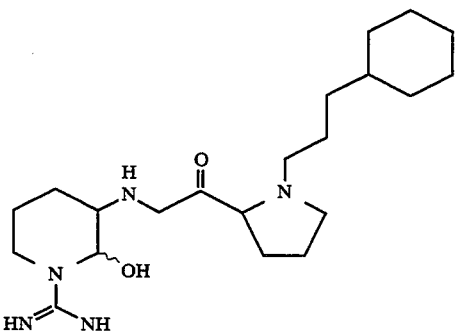

White foam, m.p. 98–105° C. (dec.); $^1$H NMR (D$_2$O) δ 5.4–5.32 (m, 1H), 3.90 (m, 1H), 3.55–3.40 (m, 2H), 3.17–3.01 (m, 2H), 2.4–2.03 (m, 4H), 1.75–1.47 (m, 2H), 1.32–1.43 (m, 4H); IR (KBr, cm$^{-1}$) 3340, 2920, 2840, 1650; MS m/z (MH+) 380.

Anal. Calcd for C$_{20}$H$_{57}$N$_2$5O$_2$·HCl·H$_2$O: C, 56.74; H, 9.24; N, 16.55.

Found: C, 57.30; H, 8.99; N, 15.06.

EXAMPLE 32

N$^\alpha$-[3-((3-phenylpropanoyl)amino)-1-benzoyl]-L-arginine aldehyde Hydrochloride Hydrate

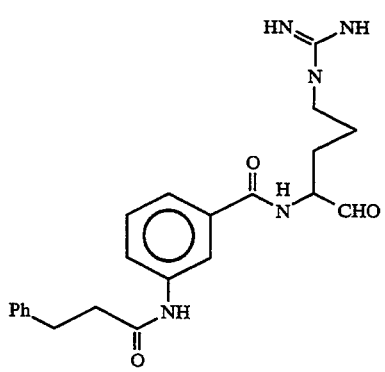

Yellow foam, m.p. 95–105° C. (dec.); $^1$H NMR (DMSO-d6) δ 10.27–10.17 (m, 1H), 8.21–7.14 (m, 9H), 3.93 (m, 1H), 3.12 (m, 1H), 2.92–2.87 (t, 2H), 2.75–2.65 (t, 2H), 1.97–1.07 (m, 4H); IR (KBr, cm$^{-1}$) 3400, 1660; MS m/z (MH+), calcd for C$_{22}$H$_{28}$N$_5$O$_3$: 410.2192, obsd 410.2184.

Other embodiments of the invention will be apparent to the skilled in the art from a consideration of this specification or practice of the invention disclosed herein. It is intended that the specification and examples be considered exemplary only, with the true scope and spirit of the invention being indicated by the following claims.

We claim:

1. A compound having the formula

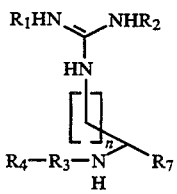

wherein

R₁ and R₂ are independently hydrogen or COOR, wherein R is hydrogen, benzyl;

R₃ is prolyl, pipecoloyl, alanyl, glycyl, or (CH₂)ₘC(O);

R₄ is R₆(CH₂)ₘC(O)—, R₆(CH₂)ₘCH(NHR₅)C(O)—, substituted or unsubstituted naphthalene sulfonyl, wherein the substituent is dialkylamino, substituted or unsubstituted 4,5-dipenyloxazol-2-yl, or 2-amino-4,5-diphenyl imidazolyl;

R₅ is aminoiminomethyl, α-aminoacetyl, substituted naphthalene sulfonyl, unsubstituted or substituted quinoline and tetrahydro quinoline sulfonyl, wherein the substituent is dialkylamino;

R₆ is hydrogen; benzyl; phenyl, phenoxy; pyridinyl; thienyl; indol-2 or 3-yl; or cycloalkyl rings of 3 to 7 carbon atoms;

R₇ is CHO n is 1, 2, 3, 4, 5, or 6; and m is 0, 1, 2, 3, or 4; or pharmaceutically acceptable salts and hydrates thereof.

2. The compound of claim 1 which is Nα-[N-(3-phenylpropanoyl)-L-propyl]-L-arginine aldehyde.

3. The intermediate Nα-[N-(3-(3-pyridyl)propanoyl)-L-prolyl]-Nδbenzyloxycarbonyl-L-arginine lactam.

4. The intermediate Nα-[N-(3-(3-pyridyl)propanoyl)-L-prolyl]-Nδ-benzyloxycarbonyl-L-arginine aldehyde.

5. The compound of claim 1 which is Nα-[N-(3-(3-pyridyl)propanoyl)-L-prolyl]-L-arginine aldehyde dihydrochloride.

6. The intermediate Nα-[N-benzoyl-L-prolyl]-Nδ-benzyloxycarbonyl-L-arginine lactam.

7. The intermediate Nα-[N-benzoyl-L-prolyl]-Nδ-benzyloxycarbonyl-L-arginine aldehyde.

8. The compound of claim 1 which is Nα-[N-benzoyl-L-prolyl]-L-arginine aldehyde hydrochloride.

9. The intermediate Nα-[N-(3-(2-thienyl)propanoyl)-L-prolyl]-Nδ-benzyloxycarbonyl-L-arginine lactam.

10. The intermediate Nα-[N-(3-(2-thienyl)propanoyl)-L-prolyl]-Nδ-benzyloxycarbonyl-L-arginine aldehyde.

11. The compound of claim 1 which is Nα-[N-(3-(2-thienyl)propanoyl)-L-prolyl]-L-arginine aldehyde hydrochloride.

12. The intermediate Nα-[N-(indole-2-carbonyl)-L-prolyl]-Nδ-benzyloxycarbonyl-L-arginine lactam.

13. The intermediate Nα-[N-(indole-2-carbonyl)-L-prolyl]-Nδ-benzyloxycarbonyl-L-arginine aldehyde.

14. The compound of claim 1 which is Nα-[N-(indole-2-carbonyl)-L-prolyl]-L-arginine aldehyde hydrochloride.

15. The intermediate Nα-[N-phenylacetyl-L-prolyl]-Nδ-benzyloxycarbonyl-L-arginine lactam.

16. The intermediate Nα-[N-phenylacetyl-L-prolyl]-Nδ-benzyloxycarbonyl-L-arginine aldehyde.

17. The compound of claim 1 which is Nα-[N-phenylacetyl-L-prolyl]-L-arginine aldehyde.

18. The intermediate Nα-[N-(3-cyclohexylpropanoyl)-L-prolyl]-Nδ-benzyloxycarbonyl-L-arginine lactam.

19. The intermediate Nα-[N-(3-cyclohexylpropanoyl)-L-prolyl]-Nδ-benzyloxycarbonyl-L-arginine aldehyde.

20. The compound of claim 1 which is Nα-[N-(3-cyclohexylpropanoyl)-L-prolyl]-L-arginine aldehyde.

21. The intermediate Nα-[N-(3-phenylpropanoyl)-L-prolyl]-Nδ-benzyloxycarbonyl-L-arginine lactam.

22. The intermediate Nα-[N-(3-phenylpropanoyl)-L-prolyl]-Nδ-benzyloxycarbonyl-L-arginine aldehyde.

23. The intermediate Nα-[N-phenoxyacetyl-L-prolyl]-Nδ-benzyloxycarbonyl-L-arginine lactam.

24. The intermediate Nα-[N-phenoxyacetyl-L-prolyl]-Nδ-benzyloxycarbonyl-L-arginine aldehyde.

25. The compound of claim 1 which is Nα-[N-phenoxyacetyl-L-prolyl]-L-arginine aldehyde.

26. The intermediate N-(N,N'-dibenzyloxycarbonylaminoiminomethyl)-D-phenylalanyl-L-proline and tert-butyl ester.

27. The intermediate N-(5-dimethylamino-1-naphthalenesulfonyl)-glycyl-L-proline tert-butyl ester.

28. The intermediate N-(5-dimethylamino-1-naphthalensulfonyl)-glycyl-L-proline.

29. The intermediate N-(8-quinolinesulfonyl)-glycyl-L-proline tert-butyl ester.

30. The intermediate N-(8-Quinolinesulfonyl)-glycyl-L-proline.

31. The intermediate Nα-[N-(3-phenyl propanoyl)-glycyl]-Nδ-benzyloxycarbonyl-L-arginine aldehyde.

32. The compound of claim 1 which is Nα-[N-(3-phenyl propanoyl)-glycyl]-L-arginine aldehyde.

33. The compound of claim 1 which is Nα-[N-(3-phenyl propanoyl)-glycyl]-L-arginine alcohol.

34. The intermediate Nα-[N-(5-dimethylamino-1-naphthalenesulfonyl)-L-prolyl]-Nδ-benzyloxycarbonyl-L-arginine lactam.

35. The intermediate Nα-[N-(5-dimethylamino-1-naphthalenesulfonyl)-L-prolyl]-Nδ-benzyloxycarbonyl-L-arginine aldehyde.

36. The compound of claim 1 which is Nα[N-(5-dimethylamino-1-naphthalenesulfonyl)-L-prolyl]-L-arginine aldehyde.

37. The intermediate (±)Nα-[N-(((3-(N-benzyloxycarbonylamino)-3-phenyl)propanoyl)-L-prolyl]-Nδ-benzyloxycarbonyl-L-arginine lactam.

38. The intermediate (±)Nα-[N-(((3-(N-benzyloxycarbonyl)amino)-3-phenyl)propanoyl)-L-prolyl ]-Nδ-benzyloxycarbonyl-L-arginine aldehyde.

39. The compound of claim 1 which is (±)Nα-[N-(3-amino-3-phenyl)propanoyl)-L-prolyl]-L-arginine aldehyde.

40. A method of inhibiting serine proteases which method comprises administering to a subject in need of such treatment, an effective amount of a compound of claim 1 or a pharmaceutically acceptable acid addition salt or hydrate thereof.

41. The method of 40 wherein the serine protease is trypsin.

42. The method of claim 40 wherein the serine protease is thrombin.

43. A pharmaceutical composition which comprises at least one compound in claim 1, or a pharmaceutically acceptable acid addition salt or hydrate thereof, in admixture with at least one pharmaceutically acceptable excipient.

44. A method of inhibiting clotting of blood in a subject in need of such treatment, which method comprises contacting said blood with an effective amount of a compound of claim 1.

45. The method of claim 44 wherein said blood is circulating within the body of the subject.

46. The method of claim 1 wherein said blood is circulating outside the body of the subject.

47. A pharmaceutical composition for inhibiting the thrombin-fibrinogen reaction containing an effective amount of a compound as defined in claim 1 as the active agent in association with a pharmaceutically acceptable carrier.

* * * * *